US012629491B2

(12) United States Patent
Li et al.

(10) Patent No.: US 12,629,491 B2
(45) Date of Patent: May 19, 2026

(54) LARYNGEAL MASK AIRWAY

(71) Applicant: CHANGSHA MAGILL MEDICAL TECHNOLOGY CO., LTD., Changsha (CN)

(72) Inventors: Daqing Li, Changsha (CN); Mijie Tang, Changsha (CN); Zhonghui Liu, Changsha (CN)

(73) Assignee: CHANGSHA MAGILL MEDICAL TECHNOLOGY CO., LTD., Changsha (CN)

( * ) Notice: Subject to any disclaimer, the term of this patent is extended or adjusted under 35 U.S.C. 154(b) by 728 days.

(21) Appl. No.: 17/427,705

(22) PCT Filed: Jan. 3, 2020

(86) PCT No.: PCT/CN2020/070293
§ 371 (c)(1),
(2) Date: Aug. 2, 2021

(87) PCT Pub. No.: WO2020/156031
PCT Pub. Date: Aug. 6, 2020

(65) Prior Publication Data
US 2022/0126042 A1 Apr. 28, 2022

(30) Foreign Application Priority Data

Feb. 2, 2019 (CN) .......................... 201910106487.4
Feb. 2, 2019 (CN) .......................... 201910106682.7
(Continued)

(51) Int. Cl.
*A61M 16/04* (2006.01)
(52) U.S. Cl.
CPC .... *A61M 16/0409* (2014.02); *A61M 16/0486* (2014.02); *A61M 16/049* (2014.02); *A61M 2205/587* (2013.01)

(58) Field of Classification Search
None
See application file for complete search history.

(56) References Cited

U.S. PATENT DOCUMENTS 6,886,561 B2 * 5/2005 Bayron ................. A61M 16/20
128/207.14
9,579,012 B2 2/2017 Vazales
(Continued)

FOREIGN PATENT DOCUMENTS

CN 2475905 Y 2/2002
CN 1878590 A 12/2006
(Continued)

OTHER PUBLICATIONS

Partial Supplementary European Search Report in the European application No. 20748256.3, mailed on Sep. 21, 2022, 13 pgs.
(Continued)

*Primary Examiner* — LaToya M Louis
(74) *Attorney, Agent, or Firm* — COOPER LEGAL GROUP LLC

(57) ABSTRACT

Provided is a laryngeal mask airway, comprising a laryngeal mask airway main body (10) and a view device (20). The laryngeal mask airway main body (10) comprises a catheter (12), and a sealing base (13) connected to the distal end of the catheter (12), and the view device (20) comprises a control part (22) and a vidicon (23), wherein an image sensor (231) is formed at the distal end of the vidicon (23), and an air guide channel (101) and a view lumen (103) are formed in the laryngeal mask airway main body (10); and a first blind end part (103a) that is closed by a light-transmitting material is formed at the distal end of the view lumen (103), the vidicon (23) is inserted into the view lumen (103) in a pluggable manner, the distal end of the view lumen (103) and the distal end of the vidicon (23) extend into the sealing base (13), and the distal end of the vidicon (23) can (Continued)

be bent and reset. The vidicon (23) is sealed inside the view lumen (103) and does not come into contact with internal tissue of a patient during use, such that the vidicon (23) can be reused in a relatively safe manner; and the distal end of the vidicon (23) can bypass the epiglottis, and the drooping epiglottis can be pushed aside by means of controlling the distal end of the vidicon (23) to be bent upwards so as to obtain a good view.

22 Claims, 16 Drawing Sheets

(30) Foreign Application Priority Data

| Feb. 2, 2019 | (CN) | .......................... 201910106849.X |
| Feb. 2, 2019 | (CN) | .......................... 201910107668.9 |

(56) References Cited

U.S. PATENT DOCUMENTS

| 9,694,150 | B2 * | 7/2017 | Brain | ................ | A61M 16/0493 |
|---|---|---|---|---|---|
| 9,889,265 | B2 * | 2/2018 | Fischer, Jr. | .......... | A61B 1/2676 |
| 9,907,919 | B2 * | 3/2018 | Dubach | ................ | A61M 16/04 |
| 9,956,367 | B1 | 5/2018 | Sun | | |
| 10,173,022 | B1 * | 1/2019 | Zachar | .............. | A61M 16/0447 |
| 10,729,866 | B2 * | 8/2020 | Cook | ................ | A61M 16/0434 |
| 10,842,962 | B2 * | 11/2020 | Brain | ................ | A61M 16/0488 |
| 2005/0279355 | A1 | 12/2005 | Loubser | | |
| 2005/0288555 | A1 | 12/2005 | Binmoeller | | |
| 2006/0004260 | A1 | 1/2006 | Boedeker | | |
| 2006/0162730 | A1 * | 7/2006 | Glassenberg | ..... | A61M 16/0436 |
| | | | | | 128/207.14 |
| 2007/0119460 | A1 * | 5/2007 | Brain | ................ | A61M 16/0425 |
| | | | | | 128/207.15 |
| 2010/0252037 | A1 | 10/2010 | Wondka | | |
| 2011/0196204 | A1 | 8/2011 | Setty | | |
| 2011/0270038 | A1 | 11/2011 | Jiang | | |
| 2012/0090609 | A1 | 4/2012 | Dubach | | |
| 2013/0035548 | A1 | 2/2013 | Ianchulev | | |
| 2013/0098367 | A1 * | 4/2013 | Chen | ..................... | A61M 16/04 |
| | | | | | 128/207.15 |
| 2013/0220332 | A1 | 8/2013 | Baska | | |
| 2013/0247917 | A1 * | 9/2013 | Brain | ................ | A61M 16/0488 |
| | | | | | 128/207.14 |
| 2014/0275772 | A1 * | 9/2014 | Chuda | ............... | A61M 16/0418 |
| | | | | | 600/104 |
| 2015/0182714 | A1 * | 7/2015 | Cook | ..................... | A61M 16/04 |
| | | | | | 128/207.15 |
| 2016/0008562 | A1 * | 1/2016 | Sagalés Mañas | . | A61M 16/0409 |
| | | | | | 128/200.26 |
| 2016/0256651 | A1 | 9/2016 | Molnar | | |
| 2017/0209022 | A1 | 7/2017 | Molnar | | |
| 2018/0169365 | A1 | 6/2018 | Sawyer et al. | | |
| 2018/0207383 | A1 * | 7/2018 | Gardner | ............ | A61M 16/0463 |
| 2020/0046926 | A1 * | 2/2020 | Kwok | ............... | A61M 16/0409 |
| 2021/0252248 | A1 | 8/2021 | William | | |

FOREIGN PATENT DOCUMENTS

| CN | 1942214 | A | 4/2007 |
|---|---|---|---|
| CN | 101374565 | A | 2/2009 |
| CN | 1859939 | B | 8/2010 |
| CN | 201739866 | U | 2/2011 |
| CN | 102283627 | A | 12/2011 |
| CN | 102448363 | A | 5/2012 |
| CN | 102475531 | A | 5/2012 |
| CN | 202408837 | U | 9/2012 |
| CN | 102783935 | A | 11/2012 |
| CN | 202569106 | U | 12/2012 |
| CN | 102872512 | A | 1/2013 |
| CN | 103075583 | A | 5/2013 |
| CN | 202937906 | U | 5/2013 |
| CN | 103180003 | A | 6/2013 |
| CN | 203075395 | U | 7/2013 |
| CN | 203620026 | U | 6/2014 |
| CN | 203656442 | U | 6/2014 |
| CN | 204351782 | U | 5/2015 |
| CN | 104800941 | A | 7/2015 |
| CN | 204446840 | U | 7/2015 |
| CN | 204533965 | U | 8/2015 |
| CN | 204582197 | U | 8/2015 |
| CN | 104976447 | A | 10/2015 |
| CN | 105050481 | A | 11/2015 |
| CN | 105156766 | A | 12/2015 |
| CN | 105343975 | A | 2/2016 |
| CN | 105407786 | A | 3/2016 |
| CN | 205215883 | U | 5/2016 |
| CN | 205252245 | U | 5/2016 |
| CN | 106178209 | A | 12/2016 |
| CN | 205814822 | U | 12/2016 |
| CN | 205947765 | U | 2/2017 |
| CN | 106793918 | A | 5/2017 |
| CN | 206138532 | U | 5/2017 |
| CN | 206167560 | U | 5/2017 |
| CN | 105050481 | B | 7/2017 |
| CN | 106999014 | A | 8/2017 |
| CN | 206443676 | U | 8/2017 |
| CN | 207119042 | U | 3/2018 |
| CN | 207356065 | U | 5/2018 |
| CN | 207614152 | U | 7/2018 |
| CN | 108653890 | A | 10/2018 |
| CN | 109091096 | A | 12/2018 |
| CN | 208370640 | U | 1/2019 |
| CN | 208405638 | U | 1/2019 |
| CN | 110292689 | A | 10/2019 |
| CN | 110292690 | A | 10/2019 |
| DE | 29825028 | U1 | 4/2004 |
| EP | 1479405 | A1 | 11/2004 |
| EP | 1738789 | B1 | 4/2011 |
| EP | 3335620 | A1 | 6/2018 |
| JP | H10-258024 | A | 9/1998 |
| JP | H11-258522 | A | 9/1999 |
| JP | 2003207655 | A | 7/2003 |
| JP | 2008528131 | A | 7/2008 |
| JP | 2010035971 | A | 2/2010 |
| JP | 2016516455 | A | 6/2016 |
| JP | 2017528194 | A | 9/2017 |
| TW | 200841855 | A | 11/2008 |
| WO | 2014135715 | A1 | 9/2014 |

OTHER PUBLICATIONS

Supplementary European Search Report in the European application No. 20748256.3, mailed on Jan. 19, 2023, 13 pgs.
International Search Report in the international application No. PCT/CN2020/070293, mailed on Mar. 26, 2020, 3 pgs.
English translation of the Written Opinion of the International Search Authority in the international application No. PCT/CN2020/070293, mailed on Mar. 26, 2020, 6 pgs.

* cited by examiner

16

12

10

13'

17

13"

151、152

21

20

22

23

N-N

LARYNGEAL MASK AIRWAY

CROSS-REFERENCE TO RELATED APPLICATIONS

The application claims priorities to the following four Chinese Patent Applications filed at the China National Intellectual Property Administration (CNIPA) on Feb. 2, 2019: 1. Chinese Patent Application No. 201910106849.X, entitled "LARYNGEAL MASK AND LARYNGEAL MASK MAIN BODY THEREOF, AND VIDEO FAR END ACCOMMODATION STRUCTURE"; 2. Chinese Patent Application No. 201910106487.4, entitled "VIDEO FAR END ACCOMMODATING ASSEMBLY, LARYNGEAL MASK MAIN BODY WITH SAME AND LARYNGEAL MASK"; 3. Chinese Patent Application No. 201910106682.7, entitled "LARYNGEAL MASK"; 4. Chinese Patent Application No. 201910107668.9, entitled "LARYNGEAL MASK AND VIEW DEVICE THEREOF", the entire contents of which are incorporated herein by reference.

TECHNICAL FIELD

The disclosure relates to the technical field of medical instruments, and in particular to a laryngeal mask airway.

BACKGROUND

In order to ensure the accuracy of an insertion position of a laryngeal mask airway, an operator usually detects the insertion position by various indirect means, such as observing expansion and reduction of the volume of chest cavity, performing auscultation for detecting sound under air leakage, monitoring End-tidal carbon dioxide partial pressure (PetCO2), etc., however, although various indirect detection means play an important role in actual operation, there are inherent limitations in the indirect manner thereof, and there is a risk of misjudgment. Therefore, if necessary, it is required to directly use a visual flexible endoscope to detect the insertion position. However, there are also problems with the direct use of the visual flexible endoscope. First, the visual flexible endoscope is a reusable instrument and directly contacts the patient's tissues, thus the disinfection requirement thereof is high and the disinfection process is relatively complicated. Second, the visual flexible endoscope is relatively expensive in cost and is not a readily available standby instrument, such as lack of the visual flexible endoscope may occur during some emergency airway process or in a part of primary medical units. Again, the visual flexible endoscope is mainly used for inspection after insertion of the laryngeal mask airway or for guiding an endotracheal tube to pass through the laryngeal mask airway into the glottis, rather than achieving visibility all the way during insertion of the laryngeal mask airway, thus it is difficult to effectively reduce repeated insertion of the laryngeal mask airway.

In the Patent published as No. CN205814822U and entitled "VISUAL INTUBATE LARYNGEAL MASK", an image sensor is disposed in an airway tube of the laryngeal mask airway, a cable or the like is disposed along an inner wall of the airway tube of the laryngeal mask airway, an outlet of the image sensor is flush with an outlet at a distal end of the airway tube, and a port is reserved at a proximal end of the cable to connect a display screen and a power supply. Such design only allows the image sensor to be fixedly embedded in the laryngeal mask airway in advance, so that components such as the image sensor and the cable, etc. are difficult to be removed and reused for other laryngeal mask airways, thus application cost of the laryngeal mask airway is high. Furthermore, when the patient's epiglottis downfolds, it may shield the image sensor, thus it is unable to acquire a complete glottis image or it is totally unable to acquire the glottis image.

In the Patent published as No. CN1859939B and entitled "INTUBATING LARYNGEAL MASK AIRWAY DEVICE WITH FIBER OPTIC ASSEMBLY", the images of the glottis and of a part of interior of a sealing dome are transmitted to an external display through a bundle of optical fibers, an operator may perform a visual operation of endotracheal intubation, the bundle of optical fibers is embedded into a sealing dome of the laryngeal mask airway in advance, an outlet position thereof is fixed and non-adjustable, and when the patient's epiglottis downfolds, the epiglottis may shield the outlet of the bundle of optical fibers, thus it is unable to display the glottis image. Furthermore, since the outlet position is fixed and non-adjustable, the scope of the glottis and its peripheral area observed by the bundle of optical fibers are relatively small and are greatly influenced by the number of the optical fibers. In addition, the bundle of optical fibers cannot be removed and the application cost thereof is relatively high.

SUMMARY

In view of this, it is desirable for the embodiments of the disclosure to provide a laryngeal mask airway having a relatively safe re-usage of a view device and a good field of view.

In order to achieve the above object, an embodiment of the disclosure provides a laryngeal mask airway including a laryngeal mask airway main body including a tubular body and a sealing dome connected to a distal end of the tubular body, and a view device including a control part and an image tube connected to the control part, a distal end of the image tube is provided with an image sensor, the laryngeal mask airway main body is formed with an airway channel and a view lumen therein; a distal end of the view lumen is formed with a first light-transmitting blind end, the image tube is inserted into the view lumen in a pluggable manner, the distal end of the view lumen and the distal end of the image tube extend into the sealing dome, and the distal end of the image tube is capable of being bent and returned to the initial state under the control of the control part.

In some implementations, the tubular body is formed with a first accommodation chamber for receiving a part of the image tube therein; the laryngeal mask airway main body includes a sealing part isolating the first accommodation chamber from a space within the sealing dome and formed with a first through hole therein, and a first hose extending at least partially into the sealing dome; a distal end of the first hose is formed as the first blind end, a proximal end of the first hose is hermetically connected to the periphery of the first through hole of the sealing part, the image tube is disposed in the first accommodation chamber and the first hose by passing through them longitudinally, and the distal end of the image tube is disposed in the first hose.

In some implementations, the first hose includes a first corrugated segment and a first rib extending along a length direction of the first corrugated segment, an inner wall of the first corrugated segment has a smooth structure, and the first rib has a thickness greater than a corresponding thickness at a trough of the first corrugated segment.

In some implementations, the first hose includes a hose main body having two open ends and a window part connected to a distal end of the hose main body, the window part has higher light-transmitting performance than that of the hose main body, and the window part is formed as the first blind end.

In some implementations, the laryngeal mask airway main body includes a light guide extending along a length direction of the image tube, a distal end of the light guide and the first blind end are disposed to be blocked mutually.

In some implementations, the laryngeal mask airway main body is formed with a light guide lumen, the light guide is preset in the light guide lumen, a distal end of the light guide lumen is formed with a second light-transmitting blind end, the distal end of the light guide lumen and the distal end of the light guide are disposed in the sealing dome, and the first blind end and the second blind end are disposed to be blocked mutually.

In some implementations, the tubular body is formed with a second accommodation chamber for receiving a part of the light guide therein, the laryngeal mask airway main body includes a second hose disposed at least partially in the sealing dome, the sealing part is formed with a second through hole therein; a distal end of the second hose is formed as the second blind end, a proximal end of the second hose is hermetically connected to the periphery of the second through hole, the light guide is disposed in the second accommodation chamber and the second hose by passing through them longitudinally, and the distal end of the light guide is disposed in the second hose.

In some implementations, the first hose includes a first corrugated segment and a first rib extending along a length direction of the first corrugated segment, an inner wall of the first corrugated segment has a smooth structure, and the first rib has a thickness greater than a corresponding thickness at a trough of the first corrugated segment.

The second hose includes a second corrugated segment and a second rib extending along a length direction of the second corrugated segment, an inner wall of the second corrugated segment has a smooth structure, and the second rib has a thickness greater than a corresponding thickness at a trough of the second corrugated segment.

In some implementations, a neutral layer of the first hose and a neutral layer of the second hose are disposed in the same neutral layer plane, and the first rib and the second rib are disposed in the neutral layer plane.

In some implementations, the distal end of the light guide is exposed within the sealing dome, and the distal end of the light guide is adhered to the first hose.

In some implementations, the distal end of the image tube is capable of making the light guide bent and returned to the initial state synchronously.

In some implementations, the distal end of the light guide is fixedly connected to the sealing dome.

In some implementations, the image tube includes a main body segment, a snake bone segment and an image segment sequentially from a proximal end to the distal end of the image tube, a distal end of the image segment is provided with the image sensor, at least a part of the snake bone segment is disposed in the sealing dome, and the distal end of the image tube is bent and returned to the initial state by the snake bone segment.

In some implementations, the control part includes a first steel wire, a second steel wire and a drive assembly, the first steel wire and the second steel wire are disposed in the image tube by passing through it longitudinally, a proximal end of the first steel wire and a proximal end of the second steel wire are driving-connected to the drive assembly respectively, a distal end of the first steel wire is connected to an inner top of a distal end of the snake bone segment, a distal end of the second steel wire is connected to an inner bottom of the distal end of the snake bone segment, and the first steel wire and the second steel wire are driven by the drive assembly to make the snake bone segment bent upward and returned to the initial state.

In some implementations, the laryngeal mask airway main body includes a transition sleeve, an interior of the first hose is formed as a first cavity, an interior of the second hose is formed as a second cavity, the transition sleeve is fixedly connected to a proximal end of the first cavity and a proximal end of the second cavity; the laryngeal mask airway main body includes a transition joint that is sleeve-connected with the transition sleeve; the transition joint is formed as a hollow structure having two open ends, and is fixedly connected to the sealing part; the proximal end of the first cavity communicates with the first through hole through the transition joint, and the proximal end of the second cavity communicates with the second through hole through the transition joint.

In some implementations, the tubular body includes a first plastic tube, a second plastic tube and a third plastic tube independent of each other; an interior of the first hose is formed as a first cavity, an interior of the second hose is formed as a second cavity, an interior of the first plastic tube forms the view lumen together with the first cavity; an interior of the second plastic tube forms the light guide lumen together with the second cavity, and an interior of the third plastic tube forms the airway channel.

In some implementations, the laryngeal mask airway main body includes a light guide extending along a length direction of the image tube, a distal end of the light guide and the first blind end are disposed to be blocked mutually, the light guide is a plastic optical fiber, the control part includes a housing formed with a light outlet therein, and a light source emitter disposed in the housing and capable of emitting visible light, and a proximal end of the light guide aligns with the light outlet.

In some implementations, the light guide includes an electroluminescent device disposed at the distal end of the light guide lumen, and an electric wire connected to the electroluminescent device and extending from the electroluminescent device to a proximal end of the light guide lumen, and the control part includes a conductive wire electrically connected to the electric wire.

The disclosure further provides another embodiment of a laryngeal mask airway including a laryngeal mask airway main body and a view device;

the view device including a housing, a light source assembly, an image tube and a display; the housing formed with a light source cavity therein, and the housing formed with a light emitting port thereon to align with a light guide of the laryngeal mask airway, the light emitting port communicating with the light source cavity and exposed to an outer surface of the housing; the light source assembly disposed in the light source cavity and emitting visible light to be emitted through the light emitting port; a proximal end of the image tube connected to the housing; the display mounted on the housing, and the image tube electrically connected to the display;

the laryngeal mask airway main body including a tubular body, a sealing dome connected to a distal end of the tubular body, and a light guide, a proximal end of the tubular body detachably connected to a bottom of the housing; the light guide and the image tube disposed to be blocked mutually, the laryngeal mask airway main body formed with a view lumen and a light guide lumen therein, the image tube inserted into the view lumen in a pluggable manner, the light guide preset in the light guide lumen, and a proximal end of the light guide aligning with the light emitting port to guide light from the light emitting port to a distal end of the light guide.

In some implementations, the light source assembly includes a light source, a reflector and a light cone, the reflector is disposed around the light source by covering it to focus light emitted by the light source to a large end of the light cone, and a small end of the light cone is disposed at the light emitting port.

In some implementations, the housing is formed with a control cavity therein, the view device includes a transmission assembly mounted in the control cavity, the proximal end of the image tube extending into the control cavity and driving-connected to the transmission assembly, and an operation handle extending from exterior of the housing into the control cavity and driving-connected to the transmission assembly, and driving, by the transmission assembly, a distal end of the image tube to be bent and returned to the initial state.

In some implementations, the view device includes a connection boss laterally extending outward from both sides of the bottom of the housing, a clamping structure disposed at a bottom of the connection boss, and a pressing part laterally disposed outside of the connection boss; the laryngeal mask airway main body includes a connection member formed at the proximal end of the tubular body and formed with a clamping slot therein, and the pressing part drives the clamping structure to lock or unlock the clamping slot.

In some implementations, the distal end of the light guide and a distal end of the image tube extend into the sealing dome, the distal end of the light guide is isolated from a space within the sealing dome, and the distal end of the image tube is isolated from the space within the sealing dome.

In the embodiments of the disclosure, the image tube is enclosed in the view lumen and does not contact the patient's tissues during usage, and the image tube may be reused relatively safely; the distal end of the image tube may bypass the epiglottis, and if necessary, the distal end of the image tube may be controlled to be bent upward, so as to push the downfolding epiglottis aside for obtaining a good view.

DETAILED DESCRIPTION

In the embodiments of the disclosure, a "proximal end" refers to a direction close to an operator and a "distal end" refers to a direction away from the operator; orientation words "up" and "down" are defined with respect to the orientations shown in any one of FIGS. 7 to 10.

Figure 2:
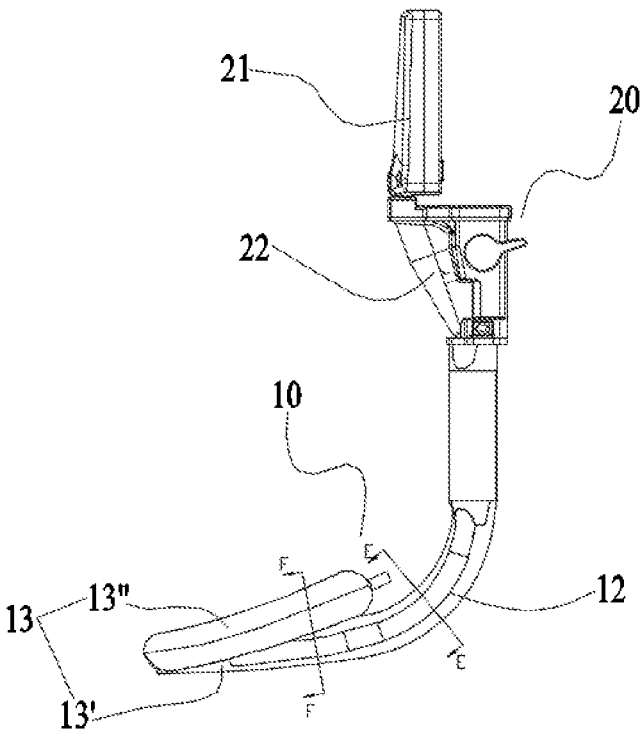
FIG. 2 is a schematic structural diagram of a laryngeal mask airway according to an embodiment of the disclosure.
Figures 3, 4:
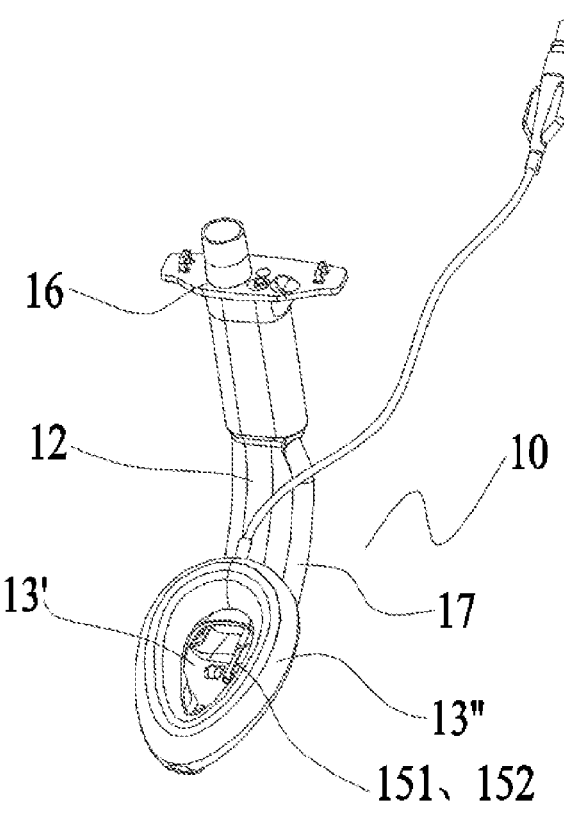
FIG. 3 is a schematic structural diagram of a laryngeal mask airway main body according to an embodiment of the disclosure.
FIG. 4 is a schematic structural diagram of a view device according to an embodiment of the disclosure.

An embodiment of the disclosure provides a laryngeal mask airway. Referring to FIGS. 2 to 4, the laryngeal mask airway includes a laryngeal mask airway main body 10 and a view device 20.

Referring to FIG. 4, the view device 20 includes a display 21, an image tube 23 and a control part 22. The image tube 23 is in the shape of an elongated tube, a distal end of the image tube 23 is provided with an image sensor 231 (referring to FIGS. 22-24), and the image tube 23 is provided with a cable (not shown in the figure) therein, and the cable may transmit an image signal collected by the image sensor 231 to the display 21. It should be noted that the display 21 itself may have signal processing capability and image display function, or may have the image display function only, and other components may perform processing on the image signal to be displayed through the display 21.

Referring to FIG. 3, the laryngeal mask airway main body 10 includes a light guide 11 (FIGS. 11 and 12), a tubular body 12, a sealing dome 13 and a gastric tube 17. The sealing dome 13 is connected to a distal outlet of the tubular body 12, a proximal end of the tubular body 12 is used to connect the view device 20 or a medical ventilator, and the gastric tube 17 extends from the proximal end of the tubular body 12 to a distal end of the sealing dome 13. It may be understood that the sealing dome 13 may be an integral structure, such as a soft structure shaped from silicone; the sealing dome 13 may also be in a structural form of a cuff dome 13' and an inflatable cuff 13"; In the embodiment of the disclosure, the sealing dome 13 is explained by example of being in the structural form of the cuff dome 13' and the inflatable cuff 13".

Figure 11:
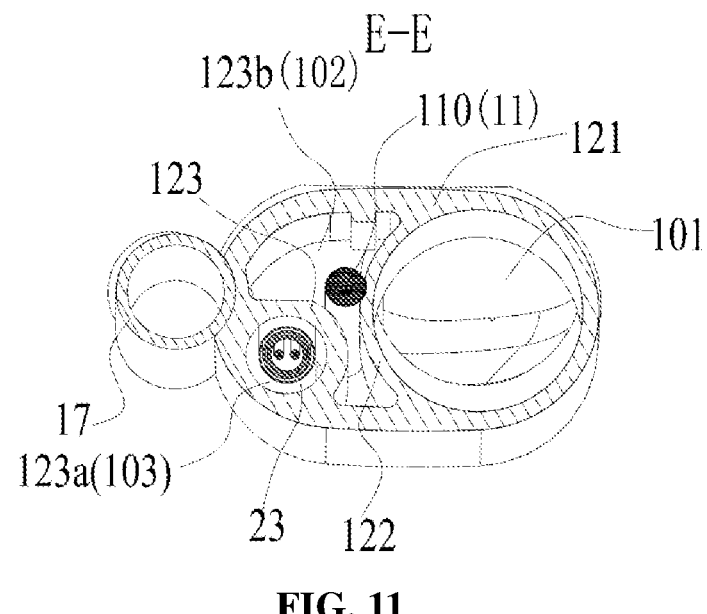
FIG. 11 is a schematic cross-sectional view taken along the E-E direction in FIG. 2.

Referring to FIG. 11, the laryngeal mask airway main body 10 is formed with an airway channel 101 and a view lumen 103 isolated from the airway channel 101 therein. Both the airway channel 101 and the view lumen 103 extend along a length direction of the tubular body 12, either from the proximal end to the distal end of the tubular body 12 or from a position along the length direction to the distal end of the tubular body 12. The view lumen 103 is isolated from the airway channel 101, and air flow does not enter the view lumen 103 during flowing into the sealing dome 13 through the airway channel 101, so that the airway channel 101 has better air-tightness, thereby allowing the air flow to be efficiently introduced into the patient' lungs. A proximal end of the view lumen 103 is formed as an open end, a distal end of the view lumen 103 is formed with a first blind end 103a formed by being enclosed by a light-transmitting material, the image tube 23 is inserted into the view lumen 103 in a pluggable manner, the distal end of the image tube 23 and the distal end of the view lumen 103 are disposed in the sealing dome 13, and the distal end of the image tube 23 may be bent and returned to the initial state. Specifically, the control part 22 may control the distal end of the image tube 23 to be bent and returned to the initial state, for example, bendable toward the upper side of the sealing dome 13.

During usage of the laryngeal mask airway according to the embodiment of the disclosure, the image tube 23 is inserted from the proximal end of the view lumen 103 to a corresponding position of the first blind end 103a of the distal end of the view lumen 103. After usage, the image tube 23 may be pulled out of the view lumen 103. The image tube 23 is enclosed in the view lumen 103 and does not contact the patient's tissues during usage, and the image tube 23 may be reused relatively safely. According to related standards, it requires the instrument reusable to be subjected to high-level disinfection after the operation when the instrument contacts the patient's tissues during the operation, and to be subjected to a general-level disinfection after the operation when the instrument does not contact the patient's tissues during the operation. In the related art, the end of the image tube 23 is exposed within the sealing dome 13, may contact the patient's in-vivo secretions and the like, and may also contact the patient's tissues such as the epiglottis 90 etc. Therefore, it requires high-level disinfection such as disinfectant immersion after the operation. In the embodiment of the disclosure, the image tube 23 does not contact the patient, and does not require an immersed disinfection or other complicated disinfection procedures, while uses low-level disinfection such as wiping, which is convenient, fast and low in cost.

Figure 8:
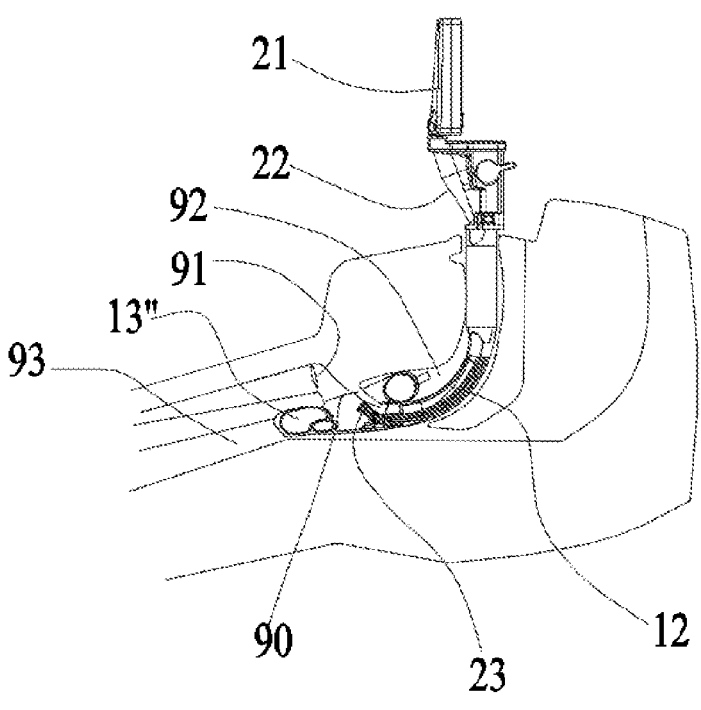
FIG. 8 is a second schematic view of a laryngeal mask airway disposed in a patient according to an embodiment of the disclosure, here the epiglottis is not downfolding and a distal end of an image tube bypasses the tip of the epiglottis and is bent upward.
Figure 9:
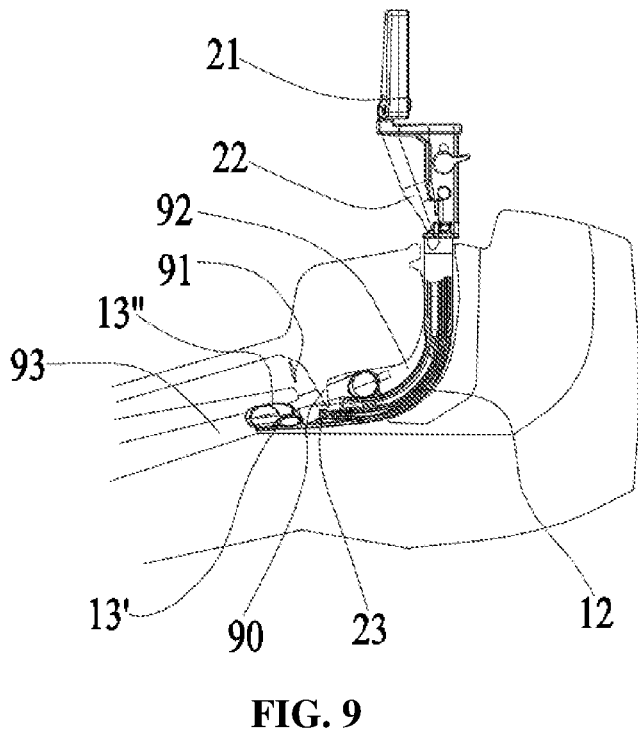
FIG. 9 is a third schematic view of a laryngeal mask airway disposed in a patient according to an embodiment of the disclosure, here the epiglottis is downfolding and a distal end of an image tube bypasses the tip of the epiglottis and is in an initial state.
Figure 10:
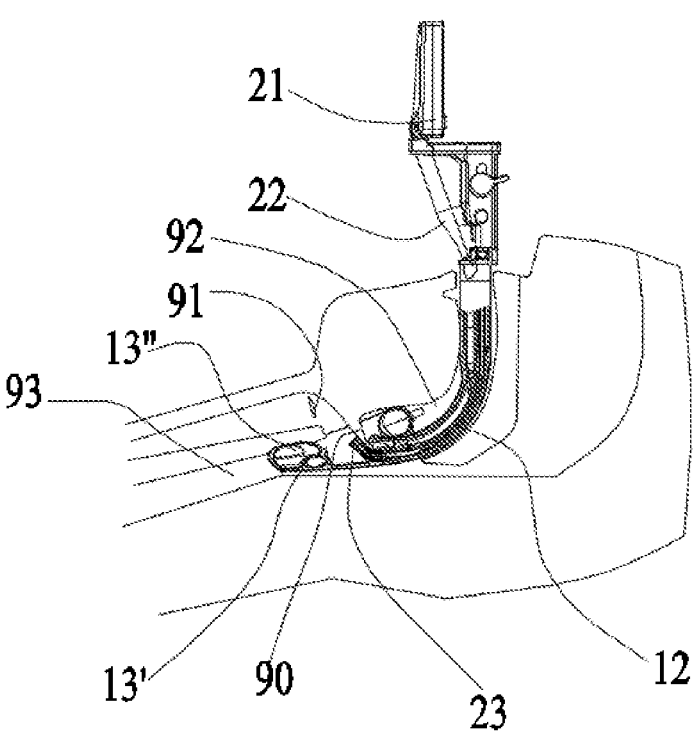
FIG. 10 is a fourth schematic view of a laryngeal mask airway disposed in a patient according to an embodiment of the disclosure, here the epiglottis is downfolding and a distal end of an image tube is bent upward to push the epiglottis aside.

In the related art, the image sensor is disposed at the junction of the sealing dome and the tubular body. When the epiglottis 90 downfolds, the epiglottis 90 may partially block the image sensor 231 from receiving the light diffusely reflected by the patient's glottis 91 and surrounding tissues. Therefore, the display 21 cannot present or may only partially present the image of the glottis 91 and surrounding tissues, and the image tube 23 and the display 21 cannot play their roles. At the moment, on one hand, alignment of the laryngeal mask airway cannot be determined accurately; on the other hand, when the endotracheal tube is required to be intubated through the laryngeal mask airway, either blind intubation is performed, which may cause injury to the patient's glottis, or trial insertion of the laryngeal mask airway is repeated with the laryngeal mask airway pulling out accordingly, which may prolong the operation time for establishing an artificial airway, increase the surgical risk, and increase the risk of injury to the patient's tissues. To this end, in the embodiment of the disclosure, when the laryngeal mask airway is inserted into the patient, the distal end of the image tube 23 bypasses the tip of the epiglottis 90. Since the distal end of the image tube 23 may be bent and returned to the initial state so that the distal end of the image tube 23 may obtain a better viewing angle of the glottis and its peripheral area, even if the epiglottis 90 downfolds, the operator may control the distal end of the image tube 23 to be bent to push the epiglottis aside, so as to obtain a better field of view. For example, referring to FIG. 7, when the epiglottis 90 does not downfold, the distal end of the image tube 23 may be kept bypassing the tip of the epiglottis 90 without bending; referring to FIG. 8, the image tube 23 may be moderately bent upward according to actual conditions to bypass the tip of the epiglottis 90, so as to obtain a better field of view. Referring to FIG. 10, when the epiglottis 90 downfolds, the operator controls the distal end of the image tube 23 to be bent upward, so as to push the epiglottis 90 aside. The operation of the embodiment is mild, the operation difficulty is small, and the risk of injury to the patient's throat tissues is low. Furthermore, the image tube 23 itself may push the epiglottis aside, and a lateral dimension of the laryngeal mask airway is not increased additionally. Therefore, during usage, the opening degree of the patient's mouth is not required to be high, and the adaptability is better. Meanwhile, in order to adjust the viewing angle direction of the distal end of the image tube 23, the bending angle at the distal end of the image tube 23 is controllable and adjustable. After the distal end of the image tube 23 is bent, the operator may control the distal end of the image tube 23 to return to the initial state as required, that is, to return to an initial state where the image tube is inserted as shown in FIG. 9.

Figure 5:
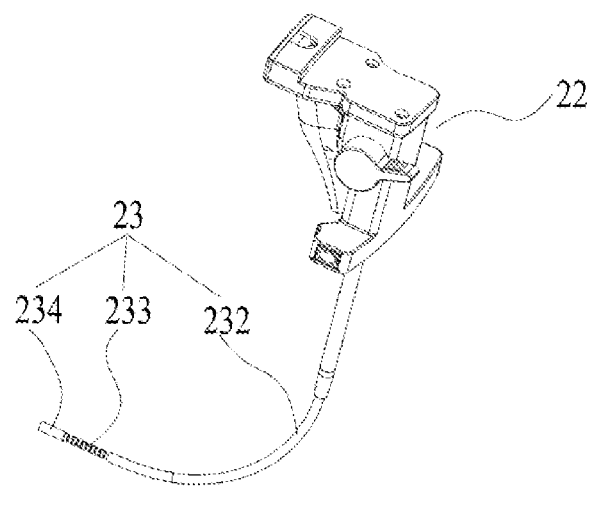
FIG. 5 is a schematic structural diagram of a part of the view device shown in FIG. 4, here a display is omitted.

Referring to FIG. 5, the image tube 23 includes a main body segment 232, a snake bone segment 233 and an image segment 234 sequentially from the proximal end to the distal end of the image tube 23, here the image sensor 231 is disposed in the image segment 234, at least a part of the snake bone segment 233 is disposed in the sealing dome 13, the snake bone segment 233 may be controlled to be bent and returned to the initial state, that is, the distal end of the image tube 23 is bent and returned to the initial state by the snake bone segment 23.

Figure 6:
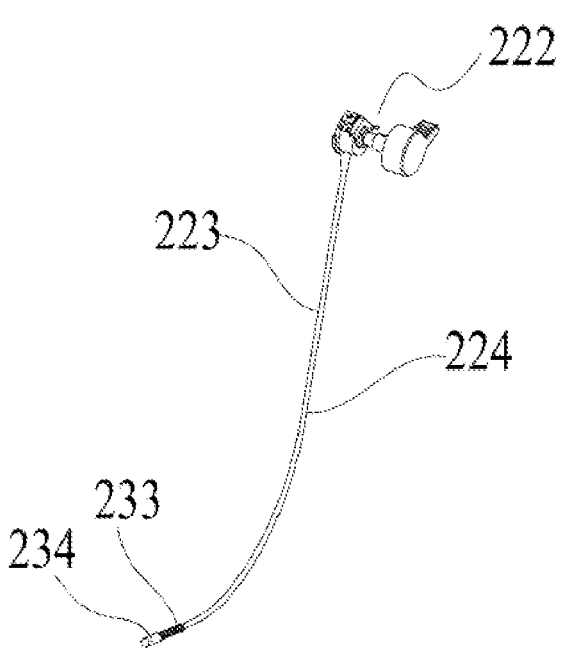
FIG. 6 is a schematic view showing a fitting structure of a drive assembly, a snake bone segment and an image segment according to an embodiment of the disclosure.
Figure 7:
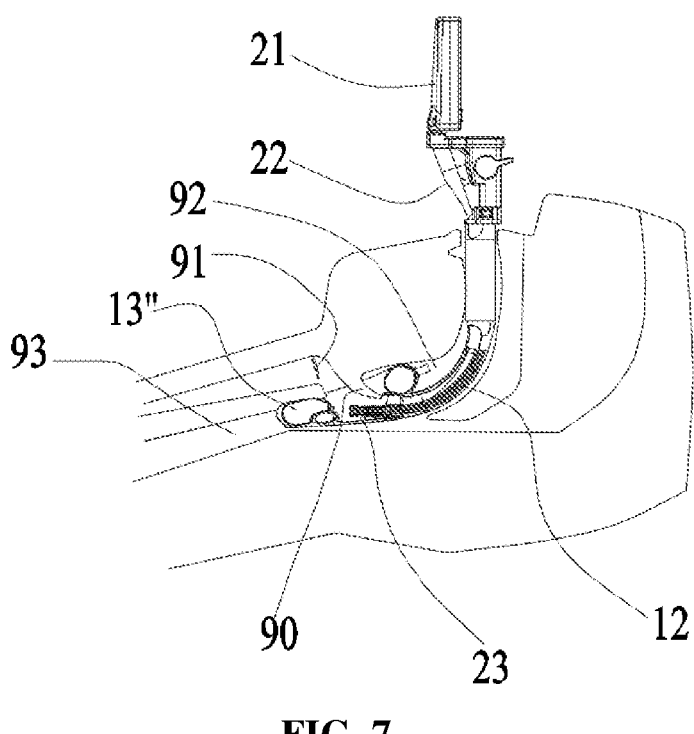
FIG. 7 is a first schematic view of a laryngeal mask airway disposed in a patient according to an embodiment of the disclosure, here the epiglottis is not downfolding and a distal end of an image tube bypasses the tip of the epiglottis and is in an initial state.

Referring to FIG. 6, the control part 22 includes a first steel wire 223, a second steel wire 224 and a drive assembly 222, here the first steel wire 223 and the second steel wire 224 are disposed in the image tube 23 by passing through it longitudinally, a proximal end of the first steel wire 223 and a proximal end of the second steel wire 224 are driving-connected to the drive assembly 222 respectively, a distal end of the first steel wire 223 is connected to an inner top of a distal end of the snake bone segment 233, a distal end of the second steel wire 224 is connected to an inner bottom of the distal end of the snake bone segment 233, that is, the first steel wire 223 and the second steel wire 224 are disposed in the snake bone segment 233 by passing through it longitudinally. When upward bending is required, the drive assembly 222 crimps the first steel wire 223 so that the effective length of the first steel wire 223 is reduced. The first steel wire 223 makes the snake bone segment 233 bent upward. When it is required to be returned to the initial state, the drive assembly 222 crimps the second steel wire 224 so that the effective length of the second steel wire 224 is reduced, meanwhile the first steel wire 223 is released, and the restoring operation of the snake bone segment 233 is achieved by the second steel wire 224. It should be noted that "top" and "bottom" described in this paragraph are defined with respect to the orientation shown in FIG. 6.

An end face of the first blind end 103*a* may be a plane or an arc surface protruding outward, for example, a spherical cap, an ellipsoidal surface or the like. Furthermore, in order to reduce large attenuation caused by light incident on the first blind end 103*a* and thus affecting the imaging effect of the image sensor 231, a material having good light-transmitting performance such as polycarbonate (PC) or polymethyl methacrylate (PMMA) may be used for the first blind end 103*a*.

The tubular body 12 is formed with a first accommodation chamber 123*a* for receiving a part of the image tube 23 therein. The tubular body 12 is not limited in structure, and may be formed by bundling multiple plastic tubes together, or may be formed as a tube structure. It should be noted that in order to ensure that the airflow may enter the sealing dome 13 and then enter the patient's lungs efficiently through the airway channel 101, it is required to ensure that the airflow entering the sealing dome 13 does not leak from the gap among the view lumen 103, the light guide lumen 102 and the airway channel 101, otherwise the airflow cannot enter the patient's lungs effectively, causing the patient to be under inadequate oxygen supply, thus risks occur. To this end, referring to FIGS. 14 and 15, the laryngeal mask airway main body of the embodiment further includes a first hose 152, a transition sleeve 155, a sealing part 154 and a transition joint 153. The sealing part 154 isolates the first accommodation chamber 123*a* in the tubular body 12 from a space within the sealing dome 13 and is formed with a first through hole 154*a* therein. A proximal end of the first hose 152 is formed as an open end, a distal end of the first hose 152 is closed by a light-transmitting material, the distal end of the first hose 152 is formed as the first blind end 103*a*, the proximal end of the first hose 152 is hermetically connected to the periphery of the first through hole 154*a* of the sealing part 154, a space within the first hose 152 is communicated with the first accommodation chamber 123*a* in the tubular body 12, and the image tube 23 is disposed in the first accommodation chamber 123*a* and the first hose 152 by passing through them longitudinally, that is, the first accommodation chamber 123*a* in the tubular body 12 and the space within the first hose 152 are co-formed as the entire view lumen 103 or a part of the view lumen 103. It should be noted that the sealing part 154 is not limited in structure, as long as it play a role of isolating the first accommodation chamber 123*a* from the space within the sealing dome 13. For example, the sealing part 154 and main tube may be formed as an integral structure. The sealing part 154 may be formed as an individual component. For example, when a part of the structure of the sealing part 154 is formed with a fabrication hole, the fabrication hole is required to be blocked with a plug, and in this case, the plug is formed as a part of the sealing part 154.

It may be understood that the first hose 152 is made of a soft material so that the first hose 152 may be relatively easily bent in synchronization with the distal end of the image tube 23, reducing the resistance formed by the first hose 152 when the image tube 23 is bent.

Figure 14:
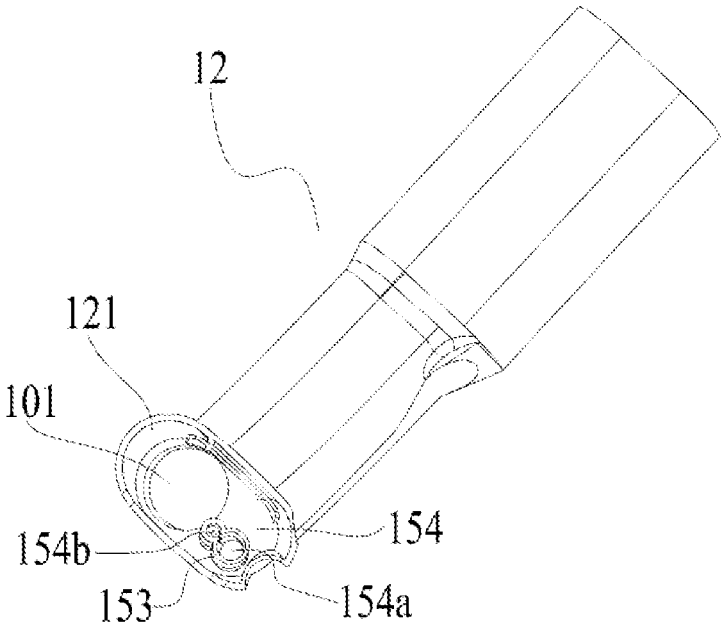
FIG. 14 is a schematic view showing a fitting structure of a tubular body, a transition joint and a sealing part according to an embodiment of the disclosure.
Figure 15:
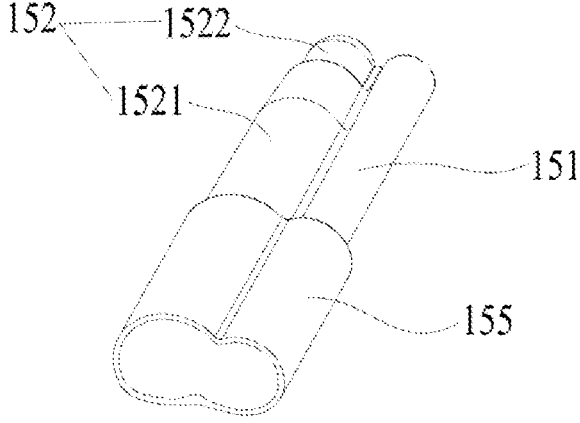
FIG. 15 is a schematic structural diagram of a first hose, a second hose and a transition sleeve according to a first embodiment of the disclosure.

Furthermore, referring to FIGS. 14 and 15, in order to improve the connection reliability between the first hose 152 and the sealing part 154, the transition sleeve 155 is fixedly connected to the proximal end of the first hose 152, for example, they are formed as an integral structure; the transition joint 153 is formed around the first through hole 154*a* of the sealing part 154 facing a side surface of the sealing dome 13, for example, they are formed as an integral structure, and the transition sleeve 155 is fixedly sleeve-connected with the transition joint 153. Specifically, the transition sleeve 155 may be sleeve-connected with an outer circumferential surface of the transition joint 153, or the transition joint 153 may be sleeve-connected with an outer circumferential surface of the transition sleeve 155, and adhesion is done where the sleeve-connection is performed. According to the embodiment of the disclosure, the solution of the transition sleeve 155 and the transition joint 153 not only increases the strength of connecting the first hose 152 and the sealing part 154 (the sleeve-connection of the transition sleeve 155 and the transition joint 153 greatly increases the adhesion area), but also ensures the sealing performance of the view lumen 103, and the reduces manufacturing difficulty.

Figure 1:
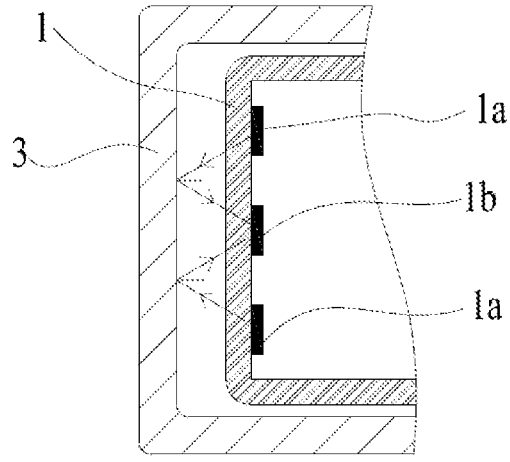
FIG. 1 is a simplified schematic structural diagram of an image tube and a transparent window in the related art.

In the related art, a light guide is integrated at an end of an image tube. Specifically, referring to FIG. 1, in the related art, the end of the image tube is integrated with a light source 1a and an image sensor 1b. The light source 1a and the image sensor 1b are disposed at a distal end of a view lumen. A transparent window 3 is disposed outside of the distal end of the view lumen. Because an image tube in the related art does not have the function of bending and returning to the initial state, an end of the image tube 1 is required to fit tightly against the transparent window 3 to avoid light reflection. When there is a gap between the end of the image tube 1 and the transparent window 3, the light emitted by the light source 1a (as indicated by the arrows in the figure) is reflected at certain angles on the inner surface of the transparent window 3, and the reflected light is directed toward the image sensor 1b, generating a light reflection effect that interferes with the imaging. Furthermore, when the epiglottis downfolds, the epiglottis easily covers the positions of the light source 1a and the image sensor 1b, and the display cannot present or may only partially present the image of the glottis and surrounding tissues. In the embodiment of the disclosure, since the end of the image tube 1 may be bent and returned to the initial state, when the light guide in the related art is integrated at the end of the image tube and when the image tube moves, it inevitably causes a gap between the end of the image tube and the transparent window, and thus improvement thereof is required. Specifically, referring to FIG. 13, the light guide 11 extends along a length direction of the laryngeal mask airway main body 10, a distal end of the light guide 11 is disposed in the sealing dome 13, and the distal end of the light guide 11 and the first blind end 103a are disposed to be blocked mutually (referring to FIGS. 22-25), which means that the distal end of the light guide 11 and the distal end of the image tube 23 disposed in the first blind end 103a are isolated from each other. The light emitted from the distal end of the light guide 11 does not directly enter the image sensor 231, and the light emitted from the distal end of the light guide 11 does not substantially enter the inner surface of the first blind end 103a, and is not reflected into the image sensor 231 so that the image sensor 231 is not interfered substantially when the image sensor 231 collects light signals diffusely reflected by the patient's tissues, which helps the image tube 23 to output a high-quality image. Meanwhile, the distal end of the image tube 23 is not provided with a light source, so that the manufacturing process of the image tube 23 may be simpler.

In an embodiment of the disclosure, the distal end of the image tube 23 may make the distal end of the light guide 11 bent and returned to the initial state synchronously, so that the direction of the light emitted by the light guide 11 may be changed synchronously with the viewing angle direction of the distal end of the image tube 23, and the light intensity required by the sensor of the image tube 23 may be ensured all the way. In the embodiment which is not shown here, the distal end of the light guide 11 is fixedly connected to the sealing dome 13, which means that there is no relative movement between the distal end of the light guide 11 and the sealing dome 13, that is, the distal end of the light guide 11 remains fixed and does not bend with the distal end of the image tube 23, and the light guide 11 provides fixed illumination for the image tube 23 to illuminate the space within the sealing dome 13 and the patient's in-vivo space in the vicinity of the opening area of the sealing dome 13. The distal end of the light guide 11 is fixedly connected to the sealing dome 13 in multiple ways. For example, the distal end of the light guide 11 is adhered or clamped to an inner surface of the sealing dome 13, and for another example, the distal end of the light guide 11 is embedded in the molded structure of the sealing dome 13.

The light guide 11 may be a plastic optical fiber 110, or may be formed as a structure in which the electroluminescent device 111 cooperates with the electric wire 112. Specifically, referring to FIG. 25, when the light guide 11 is a plastic optical fiber 110, a distal end of the plastic optical fiber 110 may be exposed within the sealing dome 13. The distal end of the plastic optical fiber 110 is adhered to an outer wall of the first hose 152, not only ensuring that the distal end of the plastic optical fiber 110 may be bent and returned to the initial state with the distal end of the image tube 23 synchronously, but also improving the safety performance of the laryngeal mask airway. Or, the distal end of the plastic optical fiber 110 is connected to the inner surface of the sealing dome 13. Specifically, when the laryngeal mask airway is used, the first hose 152 is subjected to an outward force generated along the length direction during the insertion process of the image tube 23, and the first hose 152 is bent with the bending of the image tube 23, which may cause the first hose 152 (or the window part 1522) to fall off. Although the possibility of the first hose 152 falling off is very low in both cases, the plastic optical fiber 110 plays a role of connecting to the first hose 152 to further prevent the first hose 152 from escaping from the laryngeal mask airway main body 10 and entering the patient's airway. When the light guide 11 is formed as a structure in which the electroluminescent device 111 cooperates with the electric wire 112, an outer surface of the light guide 11 requires insulation protection in order to prevent the patient from electric shock.

Figure 12:
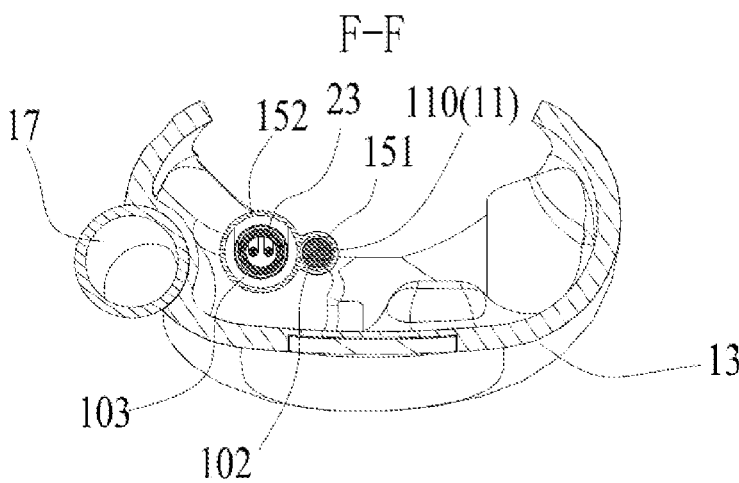
FIG. 12 is a schematic cross-sectional view taken along the F-F direction in FIG. 2.

In some embodiments of the disclosure, in order to facilitate sealing and mounting of the light guide 11, the laryngeal mask airway main body 10 is further formed with a light guide lumen 102, the light guide 11 is preset in the light guide lumen 102 (referring to FIGS. 11 and 12). Specifically, a proximal end of the light guide lumen 102 is formed as an open end, and a proximal end of the light guide 11 is exposed to the proximal end of the light guide lumen 102. In order to prevent the light guide 11 from moving along the proximal end of the light guide lumen 102, a fixing cover (not shown in the figure) may be disposed outside of the proximal end of the light guide lumen 102 to fix the proximal end of the light guide 11. A distal end of the light guide lumen 102 is formed with a second blind end 102a which is formed by being enclosed by a light-transmitting material (When the light guide 11 is a plastic optical fiber 110 and the distal end of the plastic optical fiber 110 is exposed within the sealing dome 13, the light guide lumen 102 does not have the second blind end 102a), the distal end of the light guide 11 and the distal end of the light guide lumen 102 are disposed in the sealing dome 103, and the first blind end 103a and the second blind end 102a are disposed to be blocked mutually. In the embodiment, referring to FIGS. 22-24, since the first blind end 103a and the second blind end 102a are disposed to be blocked mutually, the light in the light guide 11 (as indicated by the arrows in the FIGS. 22-24) is emitted through the second blind end 102a to illuminate a local area of the patient's tissues, and the light diffusely reflected by the patient's tissues enters the first blind end 103a, and light signals are collected by the image sensor 231 to form an image signal to be transmitted to the display 21. In an embodiment, referring to FIGS. 18 and 19, the end face of the first blind end 103a is substantially flush with an end face of the second blind end 102a along a proximal-to-distal direction. In this way, it is better to avoid interference with the image sensor 231 caused by the light emitted from the light guide 11 entering the first blind end 103*a* obliquely after passing through the second blind end 102*a*.

The view lumen 103 may be completely isolated from the light guide lumen 102, so that the insertion of the light guide 11 and the insertion of the image tube 23 do not interfere with each other, that is, the light guide 11 is not inserted into the view lumen 103 when it is inserted into the light guide lumen 102, and similarly, the image tube 23 is not inserted into the light guide lumen 102 when it is inserted into the view lumen 103, to facilitate the light guide 11 and the image tube 23 being inserted in place quickly. Generally, the image tube 23 is inserted in the preoperative process or in the first-aid site, and saving the time of inserting the image tube 23 has practical clinical significance. Of course, the view lumen 103 may also be partially isolated from the light guide lumen 102, for example, only their distal ends are isolated from each other, and the remaining channels are interconnected, that is, the channel of the view lumen 103 between its proximal end and the second blind end 102*a* and the channel of the light guide lumen 102 between its proximal end and the first blind end 103*a* are communicated.

Referring to FIGS. 15-18, in order to facilitate effective sealing of the distal end of the light guide 11, the laryngeal mask airway main body 10 according to some embodiments of the disclosure further includes a second hose 151 having a proximal end formed as an open end and a distal end closed by a light-transmitting material, and the distal end of the second hose 151 is formed as the second blind end 102*a*. The proximal end of the second hose 151 is fixedly connected to the transition sleeve 155, for example, they are formed as an integral structure, that is, the proximal end of the first hose 152 and the proximal end of the second hose 151 are integrally formed with the transition sleeve 155, thus facilitating manufacturing and processing, while ensuring the strength at the junction of the three components and the sealing performance among the three components. In the embodiment, the sealing part 154 is formed with a second through hole 154*b*, the light guide lumen 102 passes through the second through hole 154*b*, the transition joint 153 seals against the periphery of the first through hole 154*a* and the periphery of the second through hole 154*b* simultaneously, and the first hose 152 and the second hose 151 are fixedly sleeve-connected to the transition joint 153 through the transition sleeve 155.

Along a direction from a proximal end to a distal end of the laryngeal mask airway main body 10, the relative distance along the length direction between the end face of the first blind end 103*a* and the end face of the second blind end 102*a* is less than or equal to a predetermined value, which may be determined according to the dimensions of the first blind end 103*a* and the second blind end 102*a*, for example, may be 1 mm or the like. It may be understood that when the processing technique allows, the smaller the predetermined value is, the better the effect is, that is, the end face of the first blind end 103*a* is substantially flush with the end face of the second blind end 102*a*, and the end face of the first blind end 103*a* may slightly exceed the end face of the second blind end 102*a*, or the end face of the second blind end 102*a* may slightly exceed the end face of the first blind end 103*a*.

The second hose 151 is made of a soft material, such as a soft PVC. It may be understood that the space within the transition joint 153 communicating with the first hose 152 and the space within the transition joint 153 communicating with the second hose 151 may be isolated from each other or communicated with each other.

Furthermore, the first hose 152 and the second hose 151 extend at least partially into the sealing dome 13, that is, the distal end of the image tube 23 and the distal end of the light guide 11 are disposed in the sealing dome 13 so that the light guide 11 may illuminate the patient's pharyngeal cavity and its peripheral area to a large extent, including illumination of the glottis 91 and the epiglottis 90, meanwhile the distal end of the image tube 23 may also collect the image in the larger area to improve the visualization effect of the laryngeal mask airway.

It may be understood that an interior of the first hose 152 and an interior of the second hose 151 may be communicated with each other or may be isolated from each other, as long as it ensures that the first blind end 103*a* and the second blind end 102*a* are blocked mutually.

Figure 16:
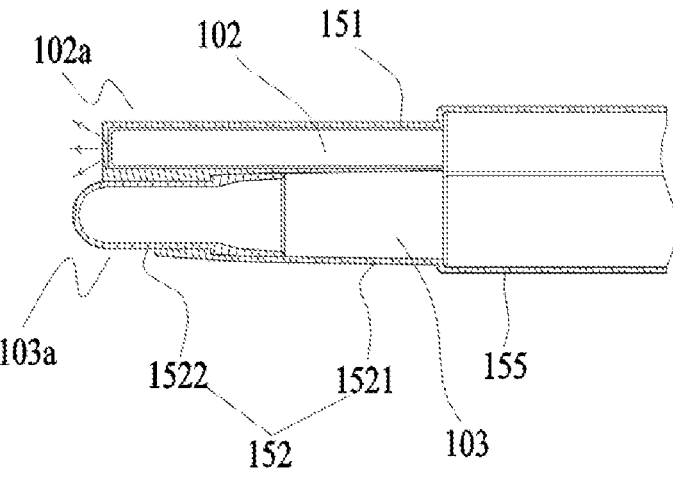
FIG. 16 is a longitudinally sectional view of the structure shown in FIG. 15.

Specifically, referring to FIGS. 15 and 16, in the structure of the first hose 152, the second hose 151 and the transition sleeve 155 according to the first embodiment of the disclosure, the first hose 152 and the second hose 151 are isolated from each other. In the embodiment, referring to FIG. 16, the first hose 152 includes a hose main body 1521 having two open ends and a window part 1522 disposed at a distal end of the hose main body 1521, the window part 1522 has higher light-transmitting performance than that of the hose main body 1521, the window part 1522 is formed as the first blind end 103*a*, and the end face of the first blind end 103*a* is formed as an arc surface protruding outward. Specifically, the window part 1522 is made of a material having better light-transmitting performance, such as PC, PMMA or the like, to ensure the light of sufficient intensity to enter the image sensor 231; the hose main body 1521 may be made of a relatively soft material, such as soft PVC, to take the bending performance of the first hose 152 into account. The window part 1522 may be disposed outside of the distal end of the hose main body 1521 by covering it; in the embodiment, a part of the structure of a proximal end of the window part 1522 extends into the hose main body 1521 and is adhered to the hose main body 1521 to enhance the connection strength there-between.

Figure 20:
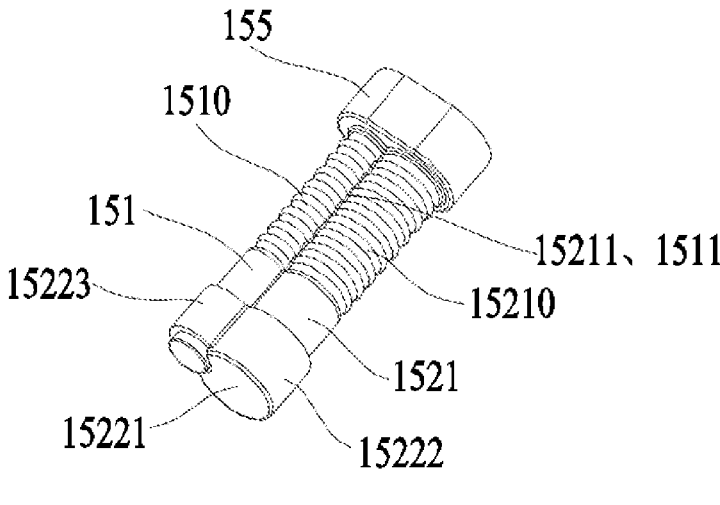
FIG. 20 is a schematic structural diagram of a first hose, a second hose and a transition sleeve according to a fifth embodiment of the disclosure.
Figure 21:
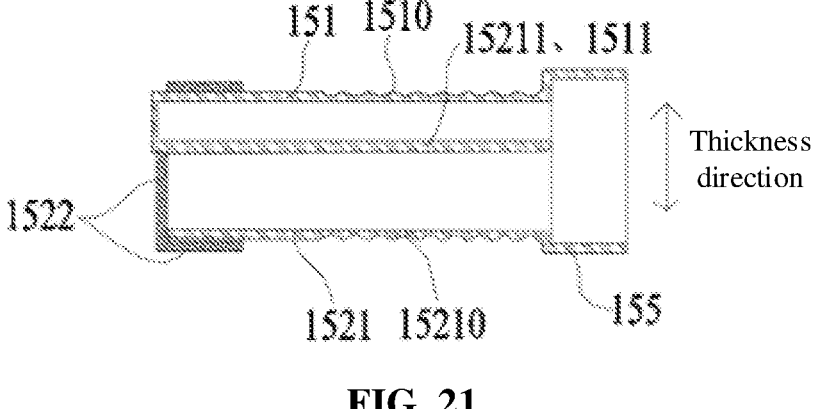
FIG. 21 is a symmetrical longitudinally sectional view of the structure shown in FIG. 20.

In another embodiment, referring to FIGS. 20 and 21, the window part includes a cover body 15221, a first sleeve part 15222 and a second sleeve part 15223. The first sleeve part 15222 extends from an edge of the cover body 15221 toward the first hose 152. An end of the first hose 152 abuts against the inside of the cover body 15221, the first sleeve part 15222 is sleeve-connected on an outer surface of the first hose 152, and the second sleeve part 15223 is sleeve-connected on an outer surface of the distal end of the second hose 151. In the window part according to the embodiment of the disclosure, the second sleeve part 15223 is sleeve-connected on the outer surface of the second hose 151 to increase the adhesive area of the window part, improve the connection reliability of the window part, and prevent the window part from falling off.

Figure 17:
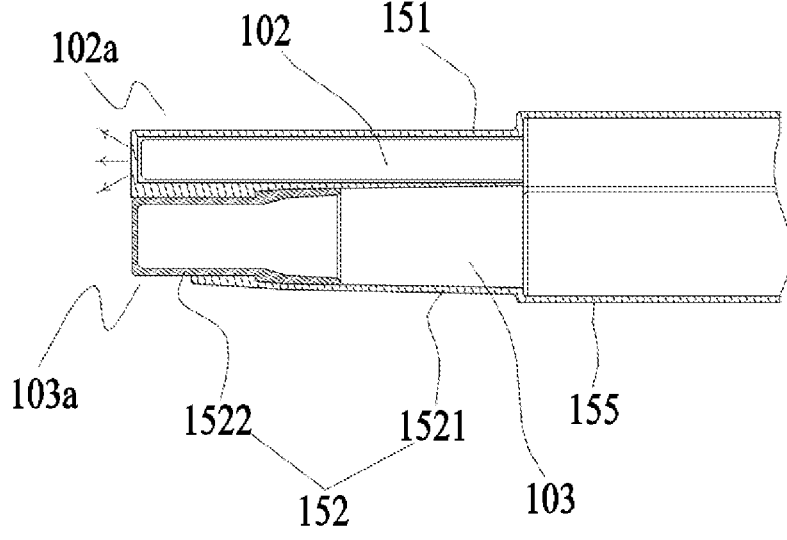
FIG. 17 is a longitudinally sectional view of a first hose, a second hose and a transition sleeve according to a second embodiment of the disclosure.

Referring to FIG. 17, the structures of the first hose 152, the second hose 151 and the transition sleeve 155 according to the second embodiment of the disclosure differ from those of the first embodiment in that in the second embodiment, the end face of the first blind end 103*a* is formed as a plane.

Figure 18:
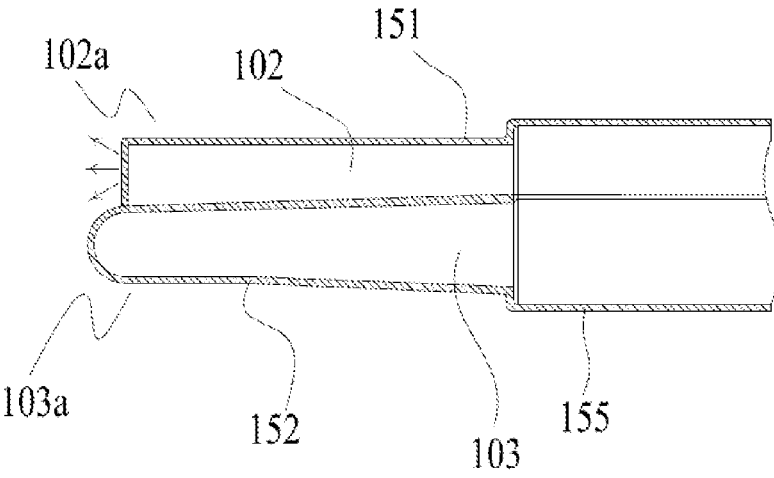
FIG. 18 is a longitudinally sectional view of a first hose, a second hose and a transition sleeve according to a third embodiment of the disclosure.

Referring to FIG. 18, in the structures of the first hose 152, the second hose 151 and the transition sleeve 155 according to the third embodiment of the disclosure, the first hose 152 and the second hose 151 are isolated from each other, the structures of the third embodiment differ from those of the first embodiment in that in the third embodiment, the first hose 152 is formed as an integral structure, that is, the first hose 152 itself has good flexibility and good light-transmitting performance. Furthermore, the first hose 152 and the second hose 151 are integrally formed to simplify manufacturing difficulty and facilitate their synchronous bending.

Figure 19:
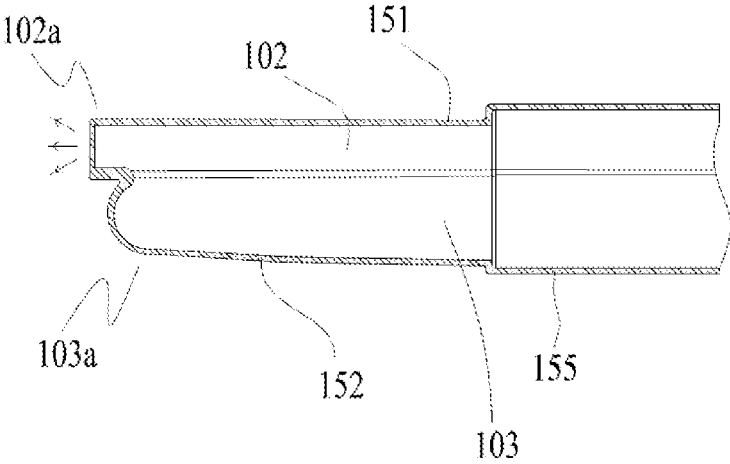
FIG. 19 is a longitudinally sectional view of a first hose, a second hose and a transition sleeve according to a fourth embodiment of the disclosure.

Referring to FIG. 19, in the structures of the first hose 152, the second hose 151 and the transition sleeve 155 according to the fourth embodiment of the disclosure, the first hose 152 and the second hose 151 are communicated with each other, and the second blind end 102*a* and the first blind end 103*a* are blocked mutually. Furthermore, in the fourth embodiment, the first hose 152 and the second hose 151 are integrally formed to simplify manufacturing difficulty and facilitate their synchronous bending.

Referring to FIGS. 20 and 21, in the structures of the first hose 152, the second hose 151 and the transition sleeve 155 according to the fifth embodiment of the disclosure, the first hose 152 includes a first corrugated segment 15210 and a first rib 15211 extending along a length direction of the first corrugated segment 15210, an inner wall of the first corrugated segment 15210 has a smooth structure, the first corrugated segment 15210 may be formed on the hose main body 1521 according to the first embodiment, the third embodiment or other embodiments, which is not limited here. The first rib 15211 has a thickness greater than a corresponding thickness at a trough of the first corrugated segment 15210; the second hose 151 includes a second corrugated segment 1510 and a second rib 1511 extending along a length direction of the second corrugated segment 1510, an inner wall of the second corrugated segment 1510 has a smooth structure, the second rib 1511 has a thickness greater than a corresponding thickness at a trough of the second corrugated segment 1510. The first corrugated segment 15210 has a crest and the trough, and the inner wall thereof has the smooth structure. Therefore, the thickness at the crest is larger than the thickness at the trough, and the crest and the trough are alternately arranged along the length direction of the first corrugated segment 15210, so that the thickness of the first corrugated segment 15210 is alternately arranged in thickness and thinness along the length direction, and similarly, the thickness of the second corrugated segment 1510 is alternately arranged in thickness and thinness along the length direction.

Taking the first corrugated segment 15210 as an example, what the smooth structure means is that the inner wall of the first corrugated segment 15210 does not have a step structure and is irrelevant of the roughness of the inner wall of the first corrugated segment 15210. That is, the inner wall of the first corrugated segment 15210 may be relatively rough, for example, has a frosted structure, or may be relatively smooth, which is not limited here.

It may be understood that during the process of forming the hose, when the thickness of the hose is thinner, the flow of the raw slurry in the mold becomes worse, the raw slurry cannot sufficiently flow to the end along the flow direction, resulting in a possible loophole in the structure at the end of the flow of the raw slurry for the hose, and thus the hose is a waste product; Or the thickness of the hose is uneven, and the thin portion of the hose is extremely thin, so that the hose is easily damaged and the quality thereof is unqualified. To this end, in the disclosure, taking the process of forming the first hose 152 as an example, in the process of injection molding the first hose 152, the raw slurry flows along the direction of the mold corresponding to the position of the first rib 15211, and the first rib 15211 is similar to the main flow path. Since the thickness of the first rib 15211 is relatively thick, that is, the space of the mold corresponding to the position of the first rib 15211 is large, the flow resistance of the raw slurry may be reduced, and the raw slurry may flow smoothly. The raw slurry flows from the position corresponding to the first rib 15211 to the positions corresponding to the crests on both lateral sides thereof, and the crest is similar to the flow branch. Since the thickness at the crest is relatively thick, the flow resistance of the raw slurry may also be reduced, so that the raw slurry may fill the position of the mold corresponding to the crest. Meanwhile, the raw slurry entering the crest of the mold may flow from the crest to both sides of the crest. The thickness of the trough is relatively thin, and the flow resistance of the raw slurry in the mold is relatively large. However, the slurry at the corresponding positions of two adjacent crests may flow to the corresponding position of the trough in the middle simultaneously. The flow distance of the raw slurry is relatively short, and the raw slurry may fully reach the corresponding position at the trough for molding.

By designing the first rib 15211, the second rib 1511 and the crest, the trough may have a thinner thickness and higher quality reliability. Because the thickness of the trough is relatively thin, the first hose 152 and the second hose 151 may have good flexibility and may be bent and returned to the initial state with the image tube synchronously. The thickness design of the first rib 15211, the second rib 1511 and the crest also increases the structural strength of the first hose 152 and the second hose 151 so that the first hose 152 and the second hose 151 do not deform during ventilating under the alternating position and negative pressures and thus block the airway channel.

Furthermore, a neutral layer of the first hose 152 and a neutral layer of the second hose 151 are disposed in the same neutral layer plane, and the first rib 15211 and the second rib 1511 are disposed in the neutral layer plane, such that the first rib 15211 and the second rib 1511 do not generate resistance to the bending of the first hose 152 and the second hose 151 substantially.

It may be understood that in an embodiment which is not shown here, when the laryngeal mask airway is not provided with the light guide, the laryngeal mask airway may include only the first hose according to any of the above-described embodiments and does not include the second hose. In the embodiment of the disclosure, the first hose 152 and the second hose 151 are formed as integral structure, the outer wall of the first hose 152 is connected to the outer wall of the second hose 151, and ribs are sandwiched between the first corrugated segment 15210 and the second corrugated segment 1510 to be connected together, that is, in this case, the first rib 15211 and the second rib 1511 are connected together.

Multiple embodiments of the laryngeal mask airway will be described in detail below with reference to the accompanying drawings.

Laryngeal Mask Airway of the First Embodiment

Referring to FIGS. 11, 12, 14 and 22, in the laryngeal mask airway according to a first embodiment of the disclosure, a tubular body 12 include a tubular main body 121, a first partition wall 122 and a second partition wall 123. The tubular main body 121 has a substantially hollow tubular shape, and the first partition wall 122 and the second partition wall 123 are disposed in the tubular main body 121 and extend along a length direction of the tubular main body 121, here the first partition wall 122 and an inner wall of the tubular main body 121 corresponding thereto are formed as an airway channel 101. When the laryngeal mask airway is required to be designed such that the endotracheal tube may be intubated, an inner wall of the airway channel 101 should be relatively smooth. For example, the cross-sectional shape of the airway channel 101 has a substantially circular shape, and the cross-section of the airway channel 101 should be dimensioned to ensure that the endotracheal tube may be intubated smoothly.

The second partition wall 123 and a corresponding portion of the tubular main body 121 are formed as a first accommodation chamber 123a, and a part of the structure of the image tube 23 is received in the first accommodation chamber 123a, that is, the first accommodation chamber 123a belongs to a part of the view lumen 103. In order to facilitate rapid insertion of the image tube 23, the cross-section of the first accommodation chamber 123a has a substantially circular shape. It may be understood that the cross-section of the first accommodation chamber 123a should be dimensioned to ensure that the image tube may pass smoothly.

Further referring to FIG. 11, a space within the tubular main body 121 except the first accommodation chamber 123a and the airway channel 101 is formed as a second accommodation chamber 123b, that is, the first partition wall 122, the second partition wall 123 and a corresponding portion of the tubular main body 121 are co-formed as the second accommodation chamber 123b, a part of the structure of the light guide 11 is received in the second accommodation chamber 123b, that is, the second accommodation chamber 123b belongs to a part of the light guide lumen 102.

Further referring to FIG. 11, the first partition wall 122 and the second partition wall 123 are arranged substantially on opposite sides along a width direction of the tubular main body 121, that is, the airway channel 101 is disposed on one side along the width direction of the tubular main body 121, and the view lumen 103 and the light guide lumen 102 are disposed on the other side along the width direction of the tubular main body 121, so that the parts of the image tube 23 and the light guide 11 within the sealing dome 13 do not affect the endotracheal intubation.

Referring to FIG. 11, a sealing part 154 is disposed at a distal end of the tubular main body 121. Specifically, the sealing part 154 is disposed at distal ends of the first accommodation chamber 123a and the second accommodation chamber 123b. The periphery of the sealing part 154 is sealing-connected with the inner wall of the tubular main body 121, for example, they are formed as an integral structure. The ends of the first partition wall 122 and the second partition wall 123 sealing-abuts against a side surface of the sealing part 154 facing away from the sealing dome 13. The sealing part 154 is formed with a first through hole 154a communicating with the first accommodation chamber 123a and a second through hole 154b communicating with the second accommodation chamber 123b therein.

Figure 22:
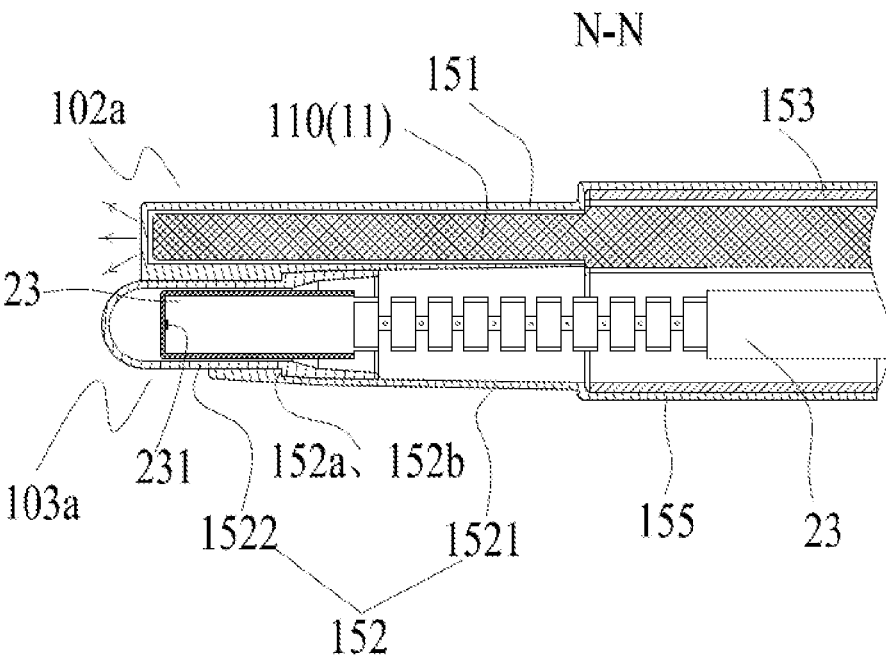
FIG. 22 is a schematic longitudinally sectional view of a part of the structure of the laryngeal mask airway taken along the N-N direction in FIG. 13 according to the first embodiment of the disclosure.

In the embodiment, referring to FIG. 22, the light guide 110 is formed as a plastic optical fiber (POF) 110 preset in the light guide lumen 102. The plastic optical fiber 110 is an optical fiber made of a highly transparent polymer, where any one or multiple of for example polystyrene (PS), polymethyl methacrylate (PMMA), polycarbonate (PC) or the like are used as a core layer material, and PMM, fluoro-plastic or the like are used as a skin layer material. The plastic optical fiber 110 is lightweight, flexible and more resistant to damage (e.g., vibration or bending); may be made by using a simple and mature polymer extruding process at a relatively low cost; has good flexibility and is easy to process and use. During usage of the laryngeal mask airway main body 10, the operator will bend the laryngeal mask airway main body 10 to varying extents to insert it into the patient's body smoothly. In the embodiment of the disclosure, the plastic optical fiber 110 is subtly applied to guide light for the laryngeal mask airway main body 10 so that the light guide 11 is not broken during the bending of the laryngeal mask airway main body 10, ensuring the reliability of the light guide 11 and the excellent illumination performance. Furthermore, the plastic optical fiber 110 of the disclosure does not have high requirements on the formula purity and the frequency band width of the raw material, so long as it is capable of guiding light and the communication function is not required, the production cost thereof may be greatly reduced, and it is particularly advantageous to popularize the application.

Figure 13:
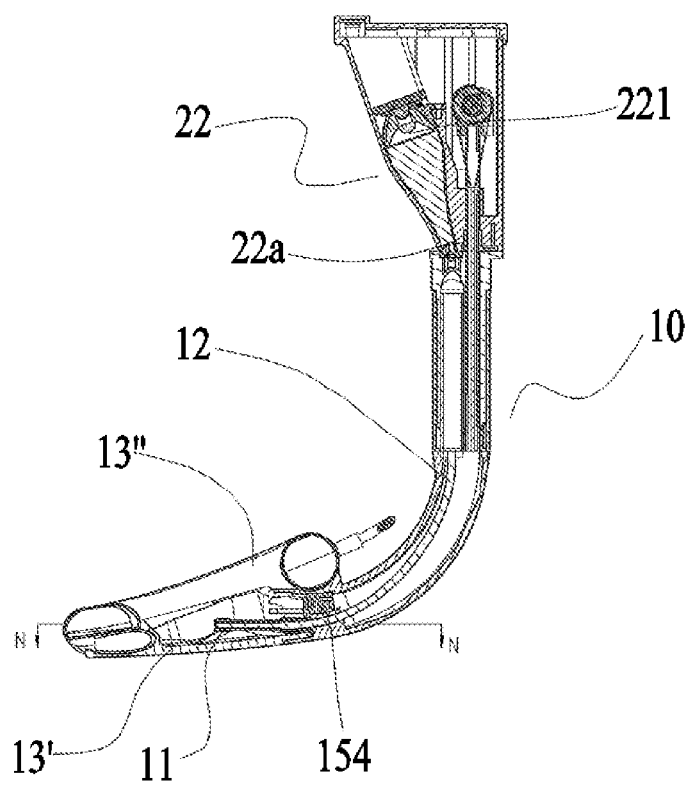
FIG. 13 is a longitudinally sectional view of the laryngeal mask airway shown in FIG. 2 (the display is omitted), here the section passes through a part of longitudinal section of light guide.

In the embodiment, referring to FIG. 13, the control part 22 includes a light source emitter 221 capable of emitting visible light and a light outlet 22a, a proximal end of the light guide 11 aligns with the light outlet 22a.

The operation procedure and working principle of the laryngeal mask airway according to the first embodiment of the disclosure are as follows.

Firstly, the image tube 23 is inserted into the view lumen 103. When the image tube 23 is inserted in place, the view device 20 and the laryngeal mask airway main body 10 are locked so that relative movement between the view device 20 and the laryngeal mask airway main body 10 does not occur. At the beginning of design, it is considered that the locking of the view device 20 and the laryngeal mask airway main body 10 may ensure the proper alignment of the light outlet 22a and the proximal end of the light guide 11. It is unnecessary to align the light outlet 22a and the proximal end of the light guide 11 deliberately, and it is time-saving and easy to operate them. The laryngeal mask airway main body 10 is connected to the view device 20. It may be understood that referring to FIG. 3, a connector 16 may be disposed at a proximal end of the laryngeal mask airway main body 10 to facilitate the locking of the view device 20 and the laryngeal mask airway main body 10.

Subsequently, the view device 20 is powered on, and the display 21 is turned on.

Then, the visualization function of the view device 20 is activated, and the light source emitter 221 outputs visible light to the proximal end of the light guide 11, and finally to the patient's tissues through the distal end of the light guide 11. Then, referring to FIG. 9, the operator gradually inserts the laryngeal mask airway main body 10 from the patient's mouth until the distal end of the laryngeal mask airway main body to abut the entrance of the esophagus 93, and image signals collected by the image sensor 231 are transmitted to the display 21. The operator may substantially determine whether the distal end of the laryngeal mask airway main body 10 is disposed in place according to the image presented on the display 21. If not, the operator should make timely adjustment to ensure that the distal end of the laryngeal mask airway main body 10 may seal the entrance of the patient's esophagus 93 to prevent gas from entering the patient' stomach. After inflation of the inflatable cuff 14, it should ensure that the inflatable cuff 14 fits and surrounds the open of the glottis 91. The distal end of the image tube 23 may bypass the epiglottis, the distal end of the image tube 23 may not be bent, or, the control part 22 of the view device 20 may be operated such that the distal end of the image tube 23 is bent upward to obtain an appropriate field of view. When the epiglottis 90 downfolds, the control part 22 may be operated to be bent upward to push the epiglottis 90 aside.

When the endotracheal intubation is not required, a medical ventilator tube joint may be directly connected to a proximal end of the airway channel 101 after the view device 20 is removed.

When the endotracheal intubation is required, the endotracheal tube is visually intubated by gradually from the proximal end to a distal end of the airway channel 101, sequentially through the sealing dome 13 and the glottis 91 to the patient's airway (the arrows in FIGS. 9 and 10 indicate the direction of directing gases to the patient's airway). The intubation may be operated visually. It should be noted that during the endotracheal intubation, the medical ventilator tube joint may be connected to the proximal end of the endotracheal tube to ventilate the patient while intubating the endotracheal tube; after the endotracheal tube is intubated in place, the medical ventilator tube joint is disconnected firstly, the view device and the laryngeal mask airway main body 10 are removed subsequently, the endotracheal tube is kept, and then the medical ventilator tube joint is connected to the proximal end of the endotracheal tube.

In other embodiments which are not shown here, a light source emitter capable of emitting visible light may be preset at a proximal end of the plastic optical fiber 110. After the view device 20 is connected to the laryngeal mask airway main body 10, a conductive wire in the view device 20 aligns with the light source emitter. When the view device 20 is activated, the visible light emitted from the light source emitter is transmitted through the proximal end to a distal end of the plastic optical fiber 110.

The laryngeal mask airway of the embodiment is illustrated by taking the structures of the first hose, the second hose and the transition sleeve in the first embodiment as an example. It should be noted that the structures of the first hose, the second hose and the transition sleeve in the second to fifth embodiments may also be used, and details thereof are not described here.

Laryngeal Mask Airway of the Second Embodiment

Figure 23:
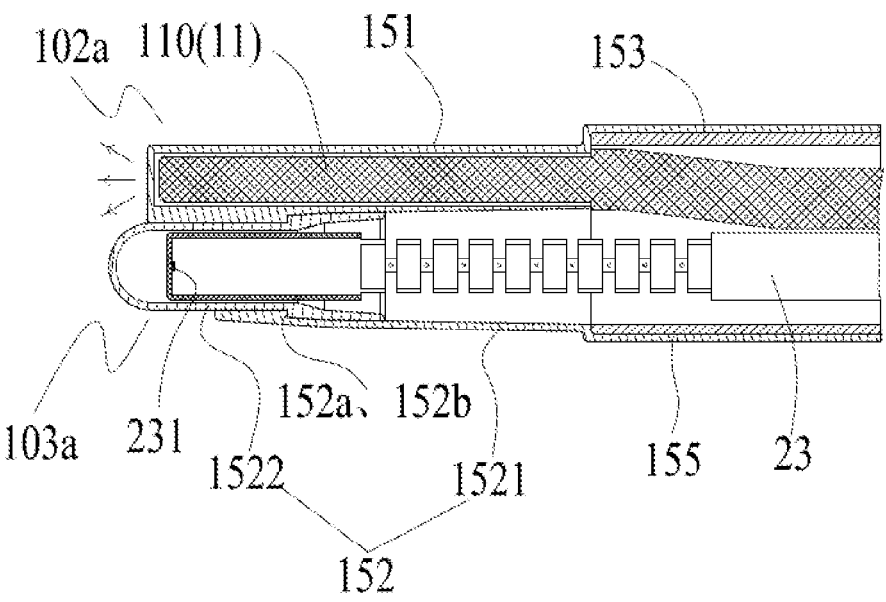
FIG. 23 is a schematic longitudinally sectional view of a part of the structure of the laryngeal mask airway taken along the same position as FIG. 22 according to the second embodiment of the disclosure.

Referring to FIG. 23, the second embodiment of the disclosure differs from the first embodiment in that the view lumen 103 and the light guide lumen 102 are communicated with each other, except the first hose 152 isolating from the second hose 151, that is, the channel of the view lumen 103 between its proximal end and a proximal end of the first hose 152 and the channel of the light guide lumen 102 between its proximal end and a proximal end of the second hose 151 are communicated with each other. Specifically, the tubular main body 121 is formed with a first partition wall 122 without a second partition wall 123 in the laryngeal mask airway of the first embodiment, and an interior of the tubular main body 121 is separated by the first partition wall 122 into two separate spaces, one of which is an airway channel 101, the other of which is formed as a compartment receiving the light guide 11 and the image tube 23 simultaneously.

Laryngeal Mask Airway of the Third Embodiment

Figure 24:
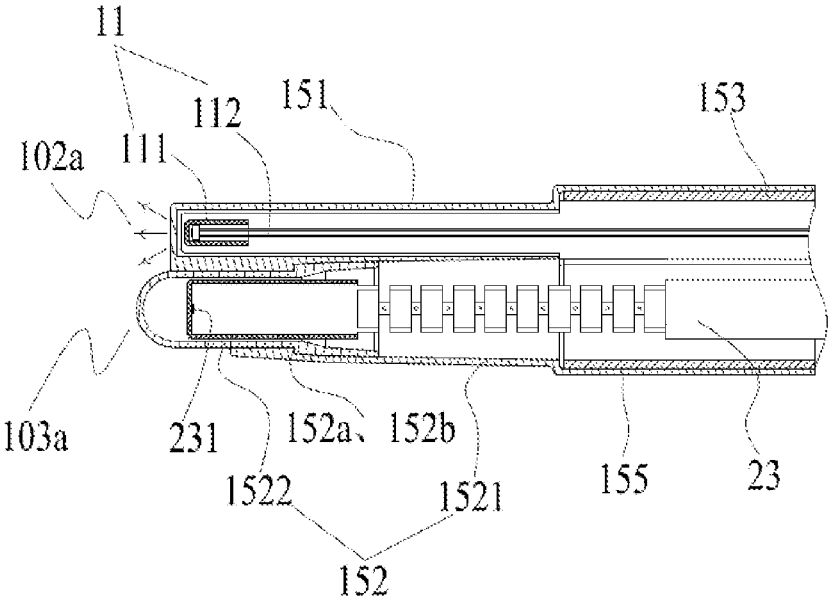
FIG. 24 is a schematic longitudinally sectional view of a part of the structure of the laryngeal mask airway taken along the same position as FIG. 22 according to the third embodiment of the disclosure.

Referring to FIG. 24, the laryngeal mask airway according to the third embodiment of the disclosure differs from the first embodiment in that the light guide 11 includes an electric wire 112 and an electroluminescent device 111. The electroluminescent device 111 refers to a device that emits light when being powered on, such as a LED lamp. The control part 22 is provided with a conductive wire (not shown in the figure). The electrical light emitter 111 is disposed at a distal end of the light guide lumen 102, the electrical wire 112 is connected to the electrical light emitter 111, and the electrical wire 112 extends along a length direction of the tubular 12 main body such that the port of the electrical wire 112 is exposed to a proximal end of the tubular main body 121. When the view device 20 is connected to the laryngeal mask airway main body 10, the conductive wire in the view device 20 aligns with the electrical wire 112, and when the view device 20 is activated, the electroluminescent device 111 is powered on to emit light, illuminating the area of the distal end of the light guide lumen 102. It should be noted that in order to facilitate the reliability of the electrical connection between the electrical wire 112 and the conductive wire, a quick-plug connector (not shown in the figure) may be disposed at an end of the tubular main body 121. When the view device 20 aligns with the laryngeal mask airway main body 10, the conductive wire in the view device 20 automatically aligns with the electrical wire 112 through the quick-plug connector. It may be understood that the structural form of the light guide 11 in the second embodiment may also be the structural form of the light guide 11 in the third embodiment.

Laryngeal Mask Airway of the Fourth Embodiment

Figure 25:
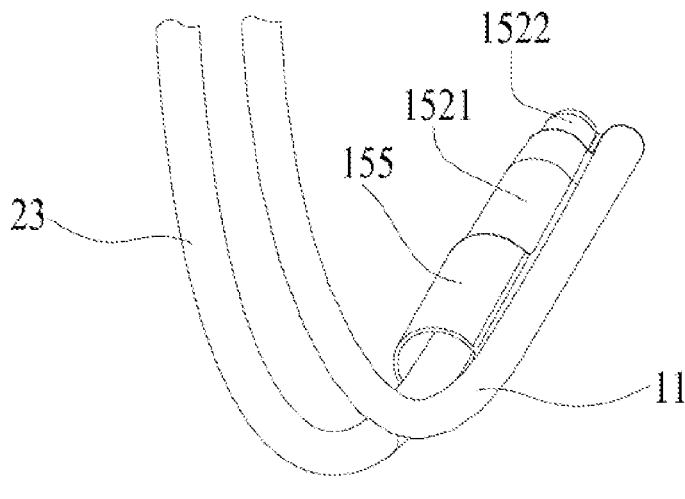
FIG. 25 is a schematic structural diagram of a part of the laryngeal mask airway according to the fourth embodiment of the disclosure.

Referring to FIG. 25, in the embodiment, the light guide 11 is formed as a plastic optical fiber 110. A distal end of the light guide 11 is exposed within the sealing dome 13, and the distal end of the light guide 11 is adhered to the first hose 152, or, the distal end of the light guide 11 is clamped to an inner surface of the sealing dome 13.

Another embodiment which is not shown here differs from the laryngeal mask airways of the first to third embodiments in that the tubular body 12 is formed by bundling multiple independent plastic tubes together, that is, the tubular body 12 includes a first plastic tube (not shown in the figure), a second plastic tube (not shown in the figure) and a third plastic tube (not shown in the figure) independent of each other, here an interior of the third plastic tube forms the airway channel 101; an interior of the first plastic tube forms the view lumen 103 together with the first cavity; an interior of the second plastic tube forms the light guide lumen 102 together with the second cavity.

Laryngeal Mask Airway of the Fifth Embodiment

Referring to FIGS. 26 to 31, the laryngeal mask airway of the fifth embodiment will be described in detail below.

The laryngeal mask airway includes a laryngeal mask airway main body 10 and a view device 20 detachably connected to the laryngeal mask airway main body 10.

Figure 26:
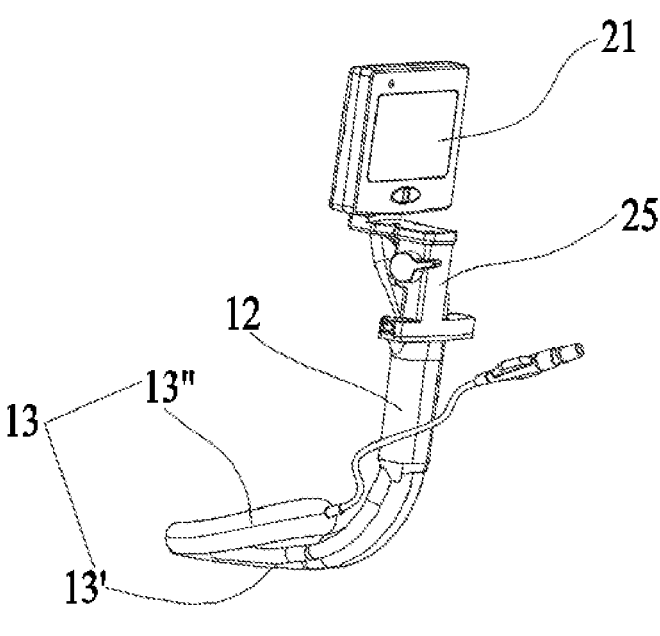
FIG. 26 is a schematic structural diagram of the laryngeal mask airway according to the fifth embodiment of the disclosure.
Figure 27:
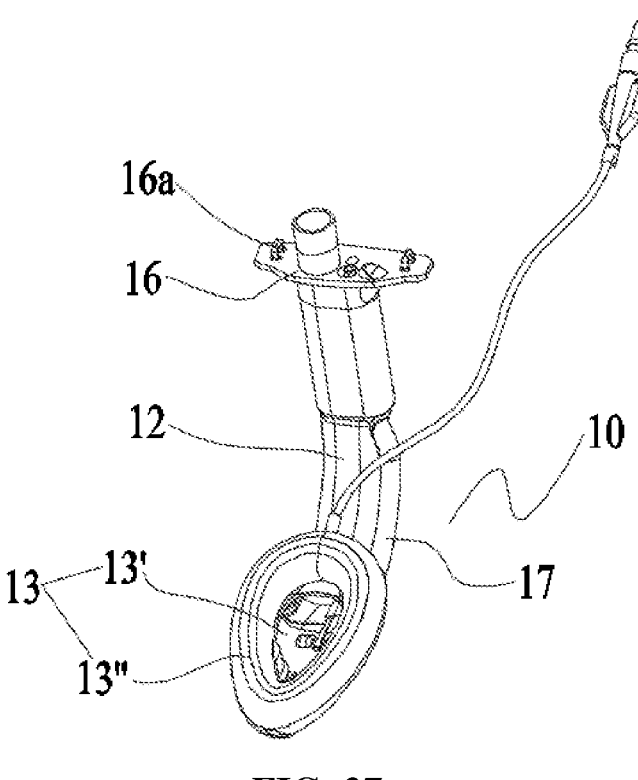
FIG. 27 is a schematic structural diagram of the laryngeal mask airway main body shown in FIG. 26.

Referring to FIGS. 26 and 27, the laryngeal mask airway main body 10 includes a light guide 11 (referring to FIG. 31), a tubular body 12, a gastric tube 17, and a sealing dome 13 connected to a distal end of the tubular body 12. The laryngeal mask airway main body 10 is formed with a light guide lumen (not shown in the figure) and a view lumen (not shown in the figure), and the light guide 11 is preset in the light guide lumen, that is, the light guide 11 is preset in the light guide lumen before the laryngeal mask airway is used. The gastric tube 17 extends from a proximal end of the tubular body 12 to a distal end of the sealing dome 13. It may be understood that the sealing dome 13 may be an integral structure or an adhered flexible structure, for example, at least a part of the structure of the sealing dome 13 is formed of a silicone material; the sealing dome 13 may also be in a structural form of a cuff dome 13' and an inflatable cuff 13"; In the embodiment, the sealing dome 13 is explained by example of being in the structural form of the cuff dome 13' and the inflatable cuff 13".

Figure 28:
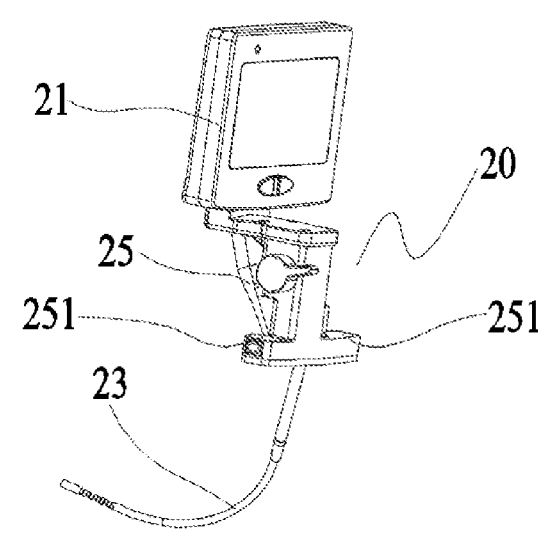
FIG. 28 is a schematic structural diagram of the view device shown in FIG. 26.
Figure 29:
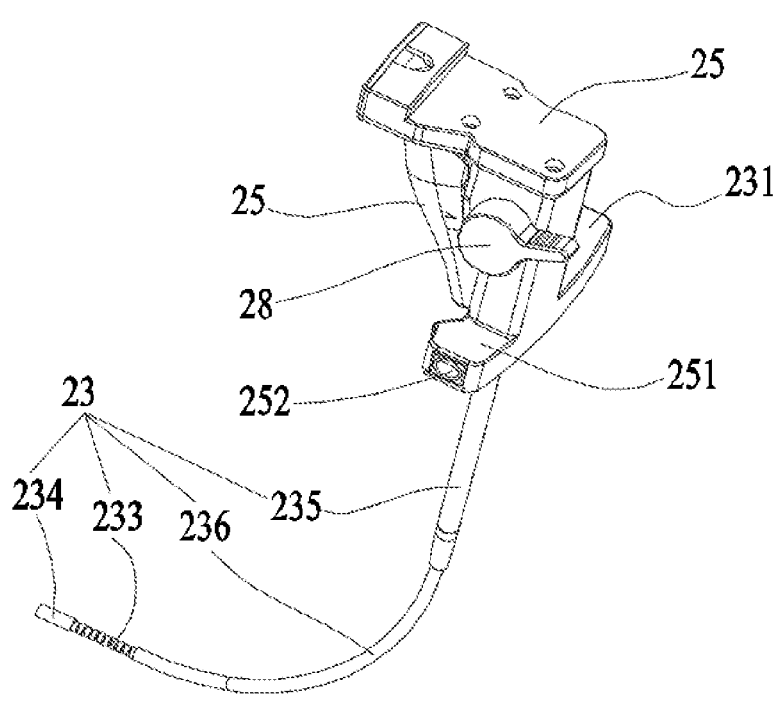
FIG. 29 is a schematic structural diagram of a part of the view device shown in FIG. 26, here a display is omitted.
Figure 30:
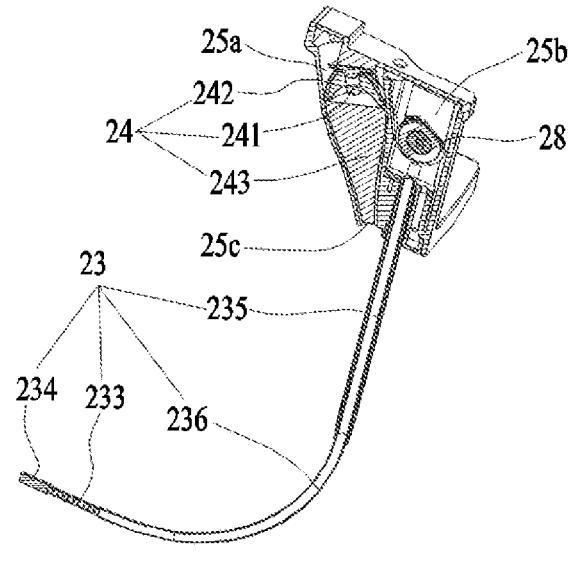
FIG. 30 is a longitudinally sectional view of the view device shown in FIG. 26.

Referring to FIGS. 28 to 31, the view device 20 includes a housing 25, a display 21, an image tube 23, a light source assembly 24, a transmission assembly and an operation handle 28. The display 21 is mounted on the housing 25, a distal end of the image tube 23 is formed with an image sensor (not shown in the figure), a proximal end of the image tube 23 is connected to the housing 25, and the image tube 23 is electrically connected to the display 21, for example, through a cable (not shown in the figure), so as to transmit the image information collected by the image tube 23 to the display 21, and the image tube 23 is inserted into the view lumen in a pluggable manner. Referring to FIG. 30, the housing 25 is formed with a light source cavity 25a and a control cavity 25b therein. The light source assembly 24 is mounted in the light source cavity 25a. The housing 25 is formed with a light emitting port 25c for aligning with a proximal end of the light guide 11 thereon, the light emitting port 25c is communicated with the light source cavity 25a and is exposed to a surface of the housing 25. When the view device 20 is connected to the laryngeal mask airway main body 10 in place, the proximal end of the light guide 11 aligns with the light emitting port 25c, and the light of the light source assembly 24 is emitted outward from a distal end of the light guide 11 after passing through the light emitting port 25c and the light guide 11 sequentially. In the view device 20 according to the embodiment of the disclosure, visible light emitted by the light source assembly 24 is transmitted to the light guide 11 through the light emitting port 25c, and the visible light in the light source assembly 24 is transmitted to a distal end of the laryngeal mask airway main body 10 through the light guide 11 so as to provide illumination for the laryngeal mask airway. That is, electric current in the light source assembly 24 does not enter the laryngeal mask airway main body 10 (the housing 25 in the view device 20 does not enter the patient), to avoid the patient from electric shock and improve safety performance of the laryngeal mask airway. Furthermore, the light emitted by the light source assembly 24 does not enter the image tube 23, but is transmitted into the light guide 11 independently, so that a light source 241 is not required to be disposed in the image tube 23, and the structure of the view device 20 is simple. Furthermore, the image tube 23 and the display 21 are connected to the housing 25, that is, the connection is not required to be re-assembled during usage of the laryngeal mask airway, the usage thereof is convenient and quick, and the view device 20 may be reused together.

Figure 31:
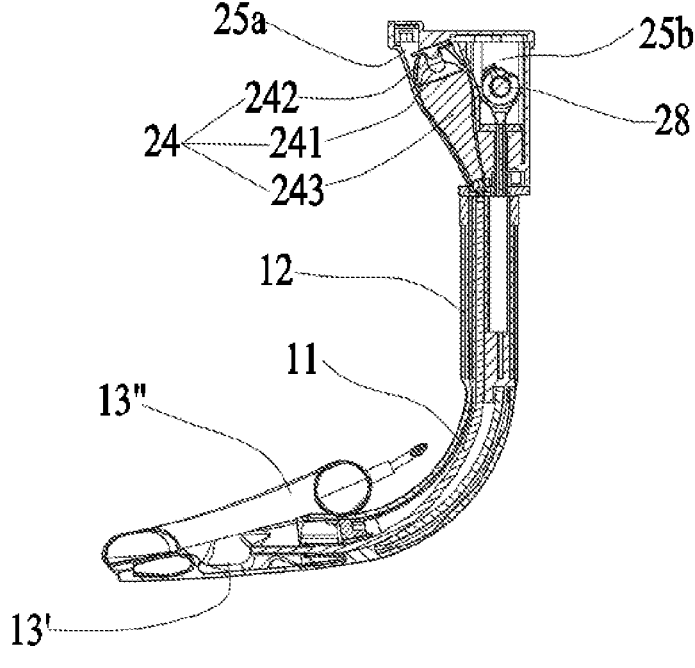
FIG. 31 is a longitudinally sectional view of a part of the structure of the laryngeal mask airway according to the fifth embodiment of the disclosure, here a display is omitted and the section passes through a part of longitudinal section of light guide.

Further referring to FIG. 31, the light source assembly 24 includes a light source 241, a reflector 242 and a light cone 243. The light source 241 may be a LED lamp or another light emitter, as long as it may emit visible light of sufficient intensity. The reflector 242 is disposed around the light source 241 by covering it to focus light emitted by the light source 241 to a large end of the light cone 243, that is, the reflector 242 plays a role of a condenser. Furthermore, in the embodiment, the reflector 242 is formed as a total reflection lens to improve the light-condensing function of the reflector 242 and reduce the loss. A small end of the light cone 243 is disposed at the light emitting port 25c, and the light travels to the small end of the light cone 243 and then is emitted from the light emitting port 25c to reduce the loss of light travelling between the small end of the light cone 243 and the light emitting port 25c. The light cone 243 may be a glass light cone 243, and further, an outer surface of the glass light cone 243 may be provided with a reflective film layer to increase the light-condensing efficiency of the glass light cone 243.

Further referring to FIG. 31, the transmission assembly is mounted in the control cavity 25b, the proximal end of the image tube 23 extends into the control cavity 25b and is driving-connected to the transmission assembly, the operation handle 28 extends from outside of the housing 25 into the control cavity 25b and is driving-connected to the transmission assembly, and the operation handle 28 drives the transmission assembly, in turn to drive the distal end of the image tube 23 to be bent and returned to the initial state. In the related art, the image sensor is disposed at the junction of the sealing dome and the tubular body, and the inflatable cuff may block a part of the viewing angle range of the image sensor. When the epiglottis downfolds, the epiglottis may block the image sensor, and the image sensor cannot collect the light diffusely reflected by the glottis and surrounding tissues, the image sensor cannot play its role, and it may be difficult to determine alignment of the laryngeal mask airway accurately. At the moment, when the endotracheal tube is required to be intubated through the laryngeal mask airway, either blind intubation is performed, which may cause injury to the patient's glottis and surrounding tissues, or trial insertion of the laryngeal mask airway is repeated with the laryngeal mask airway pulling out accordingly, which is relative troublesome, may increase the surgical risk, and increase the risk of injury to the patient's tissues. To this end, in the embodiment of the disclosure, when the laryngeal mask airway is inserted into the patient, the distal end of the image tube 23 bypasses the tip of the epiglottis 90. Since the distal end of the image tube 23 may be bent and returned to the initial state so that the distal end of the image tube 23 may obtain a better viewing angle of the glottis and its peripheral area, even if the epiglottis 90 downfolds, the operator may control the distal end of the image tube 23 to be bent to push the epiglottis aside, so as to obtain a better field of view. When the epiglottis 90 does not downfold, the distal end of the image tube 23 may be kept in its initial state, and the distal end of the image tube 23 may be moderately bent according to the actual conditions so that the image sensor obtains a better field of view. When the epiglottis 90 downfolds to block the upper area of the image tube 23, the operator rotates the operation handle to control the distal end of the image tube 23 to be bent upward, to push the epiglottis 90 aside so as to exclude the blocking of the epiglottis 90. Meanwhile, in order to adjust the viewing angle of the image sensor, the bending angle at the distal end of the image tube 23 is adjustable. After the distal end of the image tube 23 is bent, the operator may control the distal end of the image tube 23 to return to the initial state as required. The "initial state" refers to a state in which the operator does not control the bending of the image tube 23 additionally. The initial state may be a flat state or a slightly bending state of the image tube 23.

Referring to FIGS. 29 and 30, the image tube 23 includes a rigid segment 235, a flexible segment 236, a snake bone segment 233 and an image segment 234 sequentially from the proximal end to the distal end. The distal end of the image tube 23 is bent and returned to the initial state by the snake bone segment 233. An outer layer of the rigid segment 235 is formed as a sleeve rod to increase the structural strength of the image tube 23. The sleeve rod may be a metal rod or a rod made of other materials, as long as it has sufficient strength and tenacity. A part of the structure of the rigid segment 235 is inserted into the housing 25 and fixedly connected to the housing 25. The rigid segment 235 may improve the bending resistance at the connection of the image tube 23 with the housing 25 and prevent the image tube 23 from being damaged after being bent several times. The rigid segment 235 in the embodiment refers to a part of the image tube 23 that is relatively rigid and cannot be bent, and the flexible segment 236 refers to a part of the image tube 23 that is relatively flexible and may be bent. When the view device 20 and the laryngeal mask airway main body 10 are assembled, the rigid segment 235 facilitates insertion of the image tube 23 into the view lumen of the laryngeal mask airway main body 10, and the rigid segment 235 may improve the stability of mounting the view device 20; when the view device 20 is disassembled, it facilitates the operator to apply force to the rigid segment 235 so as to pull the image tube 23 out of the view lumen. During usage of the laryngeal mask airway, when it is required to adjust the position of the laryngeal mask airway in the patient's pharyngeal cavity 92, the operator holds the proximal end of the tubular body 12 and swings it back and forth to facilitate transmission of force to the tubular body 12 and the connector 16. It may be understood that the length of the rigid segment 235 is controlled, provided that it may be inserted into the patient's airway smoothly.

Referring to FIGS. 28 and 29, the view device 20 further includes a connection boss 251 extending laterally from two lateral sides of the bottom of the housing 25, a clamping structure (not shown in the figure) disposed at a bottom of the connection boss 251, and a pressing part 252 laterally disposed outside of the connection boss 251, the pressing part 252 is driving-connected to the clamping structure. In order to facilitate connecting the proximal end of the tubular body 12 to the view device 20, referring to FIG. 27, the laryngeal mask airway main body 10 includes a connection member 16 formed at the proximal end of the tubular body 12, an upper surface of the connection member 16 is formed with a clamping slot 16a for cooperating with the clamping structure, and the pressing part 252 drives the clamping structure to lock or unlock the clamping slot 16a.

In the embodiment, the light guide 11 is formed as a plastic optical fiber.

Referring to FIG. 31, the distal end of the light guide 11 and the distal end of the image tube 23 extend into the sealing dome 13, and the distal end of the light guide 11 is isolated from the space within the sealing dome 13, that is, the distal end of the light guide 11 is sealed in the light guide lumen to facilitate the sealing-installation of the light guide 11; the distal end of the image tube 23 is isolated from the space within the sealing dome 13, that is, the distal end of the image tube 23 is sealed in the view lumen so that it does not contact the patient's tissues during usage, and the image tube 23 may be reused relatively safely.

Furthermore, the distal end of the image tube 23 may make the distal end of the light guide 11 bent and returned to the initial state synchronously. In this way, the direction of the light emitted by the light guide 11 may be changed synchronously with the viewing angle direction of the distal end of the image tube 23, and the light intensity required by the image sensor may be ensured all the way.

The operation procedure and working principle of the laryngeal mask airway according to the embodiment of the disclosure are as follows.

Firstly, the image tube 23 is inserted into the view lumen. When the image tube 23 is inserted in place, the clamping structure is automatically clamped into the clamping slot 16a to lock the view device 20 and the laryngeal mask airway main body 10 so that relative movement between the view device 20 and the laryngeal mask airway main body 10 does not occur. At the moment, the light emitting port 25c is naturally disposed in the position for aligning with the proximal end of the light guide 11, thus they are not required to align deliberately, and it is time-saving and easy to operate them. The laryngeal mask airway main body 10 is connected to the view device 20.

Subsequently, the power supply (not shown in the figure) of the view device 20 is turned on, and the display 21 is turned on.

Then, the visualization function of the view device 20 is activated, and the light source 241 outputs visible light to the proximal end of the light guide 11, and finally to the patient's tissues through the distal end of the light guide 11. Then, referring to FIGS. 7 and 9, the operator gradually inserts the laryngeal mask airway main body 10 from the patient's mouth until the distal end of the laryngeal mask airway main body to abut the entrance of the esophagus 93, and image information collected by the distal end of the image tube 23 is transmitted to the display 21. When the distal end of the image tube 23 does not obtain a better field of view, the operator may rotate the operation handle to control the distal end of the image tube 23 to be bent upward to an appropriate angle. The operator may substantially determine whether the distal end of the laryngeal mask airway main body 10 is disposed in place according to the image presented on the display 21. If not, the operator should make timely adjustment to ensure that the distal end of the laryngeal mask airway main body 10 may seal the patient's esophagus 93 to prevent gas from entering the patient' stomach. After inflation of the inflatable cuff 14, it should ensure that the inflatable cuff 14 fits and surrounds the glottis opening 91. Referring to FIG. 8, when the patient's epiglottis 90 downfolds, the operation handle 28 is rotated to drive the snake bone segment 233 of the image tube 23 to be bent upward so as to push the epiglottis 90 aside.

When the endotracheal intubation is not required, the view device 20 is removed and a medical ventilator tube joint may be directly connected to the proximal end of the tubular body 12.

When the endotracheal intubation is required, the endotracheal tube is gradually intubated from the proximal end to the distal end of the laryngeal mask airway main body 10, sequentially through the sealing dome 13 and the glottis 91, the endotracheal intubation is visually operated.

The embodiments or implementations provided in the disclosure may be combined with each other without conflict.

The foregoing description is merely a preferred embodiment of the disclosure and is not intended to limit the disclosure. Various modifications and changes may be made by those skilled in the art to the disclosure. Any modifications, equivalents, modifications, etc. made within the spirit and principle of the disclosure shall fall within the protection scope of the disclosure.

The invention claimed is:

1. A laryngeal mask airway comprising:
a laryngeal mask airway main body comprising a tubular body and a sealing dome connected to a distal end of the tubular body, and
a view device comprising a control part and an image tube connected to the control part, wherein a distal end of the image tube is provided with an image sensor, the laryngeal mask airway main body being formed with an airway channel and a view lumen in the laryngeal mask airway main body; a distal end of the view lumen being formed with a first light-transmitting blind end, the image tube being inserted into the view lumen in a pluggable manner, the distal end of the view lumen and the distal end of the image tube extending into the sealing dome, and the distal end of the image tube capable of being bent and returned to an initial state under control of the control part,
wherein the laryngeal mask airway main body comprises a light guide, the first light-transmitting blind end surrounds the distal end of the image tube, and a distal end of the light guide and the first light-transmitting blind end are disposed to be optically isolated from each other, and
wherein the tubular body is formed with a first accommodation chamber for receiving a part of the image tube in the tubular body; the laryngeal mask airway main body comprises a sealing part isolating the first accommodation chamber from a space within the sealing dome and formed with a first through hole in the sealing part, and a first hose extending at least partially into the sealing dome; a distal end of the first hose is formed as the first light-transmitting blind end, a proximal end of the first hose is hermetically connected to a periphery of the first through hole of the sealing part, the image tube is disposed in the first accommodation chamber and the first hose by passing through the first accommodation chamber and the first hose longitudinally, and the distal end of the image tube is disposed in the first hose.

2. The laryngeal mask airway of claim 1, wherein the first hose comprises a first corrugated segment and a first rib extending along a length direction of the first corrugated segment, an inner wall of the first corrugated segment has a smooth structure, and the first rib has a thickness greater than a corresponding thickness at a trough of the first corrugated segment.

3. The laryngeal mask airway of claim 1, wherein the first hose comprises a hose main body having two open ends and a window part connected to a distal end of the hose main body, the window part has higher light-transmitting performance than that of the hose main body, and the window part is formed as the first light-transmitting blind end.

4. The laryngeal mask airway of claim 1, wherein the light guide extends along a length direction of the image tube.

5. The laryngeal mask airway of claim 4, wherein the laryngeal mask airway main body is formed with a light guide lumen, the light guide is preset in the light guide lumen, a distal end of the light guide lumen is formed with a second light-transmitting blind end, the distal end of the light guide lumen and the distal end of the light guide are disposed in the sealing dome, and the first light-transmitting blind end and the second light-transmitting blind end are disposed to be optically isolated from each other.

6. The laryngeal mask airway of claim 5, wherein the tubular body is formed with a second accommodation chamber for receiving a part of the light guide in the tubular body, the laryngeal mask airway main body comprises a second hose disposed at least partially in the sealing dome, the sealing part is formed with a second through hole in the sealing part; a distal end of the second hose is formed as the second light-transmitting blind end, a proximal end of the second hose is hermetically connected to a periphery of the second through hole, the light guide is disposed in the second accommodation chamber and the second hose by passing through the second accommodation chamber and the second hose longitudinally, and the distal end of the light guide is disposed in the second hose.

7. The laryngeal mask airway of claim 6, wherein the first hose comprises a first corrugated segment and a first rib extending along a length direction of the first corrugated segment, an inner wall of the first corrugated segment has a smooth structure, and the first rib has a thickness greater than a corresponding thickness at a trough of the first corrugated segment;

the second hose comprises a second corrugated segment and a second rib extending along a length direction of the second corrugated segment, an inner wall of the second corrugated segment has a smooth structure, and the second rib has a thickness greater than a corresponding thickness at a trough of the second corrugated segment.

8. The laryngeal mask airway of claim 7, wherein a neutral layer of the first hose and a neutral layer of the second hose are disposed in a same neutral layer plane, and the first rib and the second rib are disposed in the neutral layer plane.

9. The laryngeal mask airway of claim 6, wherein the laryngeal mask airway main body comprises a transition sleeve, an interior of the first hose is formed as a first cavity, an interior of the second hose is formed as a second cavity, the transition sleeve is fixedly connected to a proximal end of the first cavity and a proximal end of the second cavity; the laryngeal mask airway main body comprises a transition joint that is sleeve-connected with the transition sleeve; the transition joint is formed as a hollow structure having two open ends, and is fixedly connected to the sealing part; the proximal end of the first cavity communicates with the first through hole through the transition joint, and the proximal end of the second cavity communicates with the second through hole through the transition joint.

10. The laryngeal mask airway of claim 6, wherein the tubular body comprises a first plastic tube, a second plastic tube and a third plastic tube independent of each other; an interior of the first hose is formed as a first cavity, an interior of the second hose is formed as a second cavity, an interior of the first plastic tube forms the view lumen together with the first cavity; an interior of the second plastic tube forms the light guide lumen together with the second cavity, and an interior of the third plastic tube forms the airway channel.

11. The laryngeal mask airway of claim 5, wherein the light guide comprises an electroluminescent device disposed at the distal end of the light guide lumen, and an electric wire connected to the electroluminescent device and extending from the electroluminescent device to a proximal end of the light guide lumen, and the control part comprises a conductive wire electrically connected to the electric wire.

12. The laryngeal mask airway of claim 4, wherein the distal end of the light guide is exposed within the sealing dome, and the distal end of the light guide is adhered to the first hose.

13. The laryngeal mask airway of claim 4, wherein the distal end of the image tube is capable of making the light guide be bent and returned to the initial state synchronously.

14. The laryngeal mask airway of claim 4, wherein the distal end of the light guide is fixedly connected to the sealing dome.

15. The laryngeal mask airway of claim 1, wherein the image tube comprises a main body segment, a flexible segment and an image segment sequentially from a proximal end to the distal end of the image tube, a distal end of the image segment is provided with the image sensor, at least a part of the flexible segment is disposed in the sealing dome, and the distal end of the image tube is bent and returned to the initial state by the flexible segment.

16. The laryngeal mask airway of claim 15, wherein the control part comprises a first steel wire, a second steel wire and a drive assembly, the first steel wire and the second steel wire are disposed in the image tube by passing through the image tube longitudinally, a proximal end of the first steel wire and a proximal end of the second steel wire are driving-connected to the drive assembly respectively, a distal end of the first steel wire is connected to an inner top of a distal end of the flexible segment, a distal end of the second steel wire is connected to an inner bottom of the distal end of the flexible segment, and the first steel wire and the second steel wire are driven by the drive assembly to make the flexible segment be bent upward and returned to the initial state.

17. The laryngeal mask airway of claim 1, wherein the light guide extends along a length direction of the image tube, the light guide is a plastic optical fiber, the control part comprises a housing formed with a light outlet in the control part, and a light source emitter disposed in the housing and capable of emitting visible light, and a proximal end of the light guide aligns with the light outlet.

18. A laryngeal mask airway comprising a laryngeal mask airway main body and a view device;

the view device comprising a housing, a light source assembly, an image tube and a display; the housing formed with a light source cavity in the housing, and the housing formed with a light emitting port on the housing to align with a light guide of the laryngeal mask airway, the light emitting port communicating with the light source cavity and exposed to an outer surface of the housing; the light source assembly disposed in the light source cavity and emitting visible light to be emitted through the light emitting port; a proximal end of the image tube connected to the housing; the display mounted on the housing, and the image tube electrically connected to the display;

the laryngeal mask airway main body comprising a tubular body, a sealing dome connected to a distal end of the tubular body, and the light guide, a proximal end of the tubular body detachably connected to a bottom of the housing; the laryngeal mask airway main body formed with a view lumen and a light guide lumen in the laryngeal mask airway main body, the image tube inserted into the view lumen in a pluggable manner, the light guide preset in the light guide lumen, and a proximal end of the light guide aligning with the light emitting port to guide light from the light emitting port to a distal end of the light guide, a distal end of the view lumen formed with a first light-transmitting blind end surrounding a distal end of the image tube, and the distal end of the light guide and the first light-transmitting blind end disposed to be optically isolated from each other.

19. The laryngeal mask airway of claim 18, wherein the light source assembly comprises a light source, a reflector and a light cone, the reflector is disposed around the light source by covering the light source to focus light emitted by the light source to a large end of the light cone, and a small end of the light cone is disposed at the light emitting port.

20. The laryngeal mask airway of claim 18, wherein the housing is formed with a control cavity in the housing, the view device comprises a transmission assembly mounted in the control cavity, the proximal end of the image tube extending into the control cavity and driving-connected to the transmission assembly, and an operation handle extending from exterior of the housing into the control cavity and driving-connected to the transmission assembly, and driving, by the transmission assembly, a distal end of the image tube to be bent and returned to an initial state.

21. The laryngeal mask airway of claim 18, wherein the view device comprises a connection boss laterally extending outward from both sides of the bottom of the housing, a clamping structure disposed at a bottom of the connection boss, and a pressing part laterally disposed outside of the connection boss; the laryngeal mask airway main body comprises a connection member formed at the proximal end of the tubular body and formed with a clamping slot in the connection member, and the pressing part drives the clamping structure to lock or unlock the clamping slot.

22. The laryngeal mask airway of claim 18, wherein the distal end of the light guide and a distal end of the image tube extend into the sealing dome, the distal end of the light guide is isolated from a space within the sealing dome, and the distal end of the image tube is isolated from the space within the sealing dome.

* * * * *